(12) United States Patent
Huang et al.

(10) Patent No.: US 12,049,467 B2
(45) Date of Patent: Jul. 30, 2024

(54) SUBSTITUTED BENZOPYRAZOLO[1,5-A][1,4]DIAZEPINES AS GABA POSITIVE ALLOSTERIC MODULATORS

(71) Applicants: The Johns Hopkins University, Baltimore, MD (US); Lieber Institute, Inc., Baltimore, MD (US)

(72) Inventors: Yifang Huang, Lansdale, PA (US); Pankaj Jay Pasricha, Ellicott City, MD (US); James C. Barrow, Arnold, MD (US); Ingrid Buchler, Baltimore, MD (US); Michael Poslusney, Baltimore, MD (US)

(73) Assignees: The Johns Hopkins University, Baltimore, MD (US); Lieber Institute, Inc., Baltimore, MD (US)

( * ) Notice: Subject to any disclaimer, the term of this patent is extended or adjusted under 35 U.S.C. 154(b) by 0 days.

(21) Appl. No.: 17/590,404

(22) Filed: Feb. 1, 2022

(65) Prior Publication Data
US 2022/0251090 A1    Aug. 11, 2022

Related U.S. Application Data

(60) Provisional application No. 63/144,707, filed on Feb. 2, 2021.

(51) Int. Cl.
| | | |
|---|---|---|
| *A61K 31/5517* | (2006.01) | |
| *A61P 1/12* | (2006.01) | |
| *C07D 487/04* | (2006.01) | |
| *C07D 487/14* | (2006.01) | |

(52) U.S. Cl.
CPC .............. *C07D 487/04* (2013.01); *A61P 1/12* (2018.01)

(58) Field of Classification Search
CPC .......................... A61K 31/5517; C07D 487/14
USPC .......................................... 514/220; 540/586
See application file for complete search history.

(56) References Cited

U.S. PATENT DOCUMENTS

| | | | |
|---|---|---|---|
| 4,130,716 | A | 12/1978 | Gilman et al. |
| 4,450,150 | A | 5/1984 | Sidman |
| 8,530,438 | B2 | 9/2013 | Zamore et al. |
| 10,266,534 | B2 | 4/2019 | Pasricha et al. |
| 10,844,070 | B2 | 11/2020 | Pasricha et al. |
| 11,136,322 | B2 | 10/2021 | Pasricha et al. |
| 2017/0197967 | A1 | 7/2017 | Pasricha et al. |
| 2020/0062759 | A1 | 2/2020 | Pasricha et al. |
| 2020/0181155 | A1 | 6/2020 | Pasricha et al. |
| 2021/0163490 | A1 | 6/2021 | Pasricha et al. |

FOREIGN PATENT DOCUMENTS

| | | |
|---|---|---|
| EP | 3160969 | 5/2017 |
| JP | 6715830 | 7/2020 |
| JP | 6855615 | 4/2021 |
| WO | WO 2015200766 | 12/2015 |
| WO | WO 2020198275 | 10/2020 |

OTHER PUBLICATIONS

Jordan, V. C. Nature Reviews: Drug Discovery, 2, 2003, 205.*
Hackam, et al. JAMA, 296(14), 2006, 1731-1732.*
Bagal et al., "Minimizing Drug Exposure in the CNS while Maintaining Good Oral Absorption," Acs Medicinal Chemistry Letters, 2012, 3(12):948-950.
Capra et al., "Innovative Approach for Interstitial Cystitis: Vaginal Pessaries Loaded Diazepam—A Preliminary Study," Journal of Pharmaceutics, Jan. 20, 2013, pp. 1-7.
Everhart, "The burden of digestive diseases in the United States," NIH Publication No. 09-6443, Jan. 2008, 192 pages.

(Continued)

*Primary Examiner* — Douglas M Willis
(74) *Attorney, Agent, or Firm* — Fish & Richardson P.C.

(57) ABSTRACT

This disclosure features chemical entities (e.g., a compound or a pharmaceutically acceptable salt thereof, or an N-oxide thereof) of formula (I), which are positive allosteric modulators of one or more GABA-A receptors, e.g., which are peripherally restricted, positive allosteric modulators of one or more GABA-A receptors; e.g., which are positive allosteric modulators of one or more GABA-A receptors and which selectively target the peripheral nervous system and organs of the body, and which do not substantially pass through the blood-brain barrier. Said compounds are useful e.g., for the treatment of systemic diseases of the body, e.g., diseases in which modulation of one or more peripherally restricted GABA-A receptors is beneficial (e.g., diseases or disorders which are mediated by GABA-A neuronal activity. This disclosure also features pharmaceutical compositions containing the chemical entities described herein as well as methods of using same for the treatment of systemic diseases of the body.

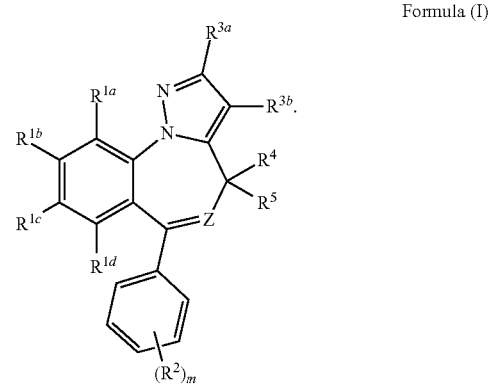

Formula (I)

25 Claims, No Drawings

(56) References Cited

OTHER PUBLICATIONS

Fargeas et al., "Central and peripheral action of GABAA and GABAB agonists on small intestine motility in rats," European Journal of Pharmacology, May 1988, 150(1-2):163-169.

Gershon, "Serotonin and its implication for the management of irritable bowel syndrome," Rev Gastroenterol Disord, Jan. 2003;3 Suppl 2:S25-34.

Grider, "Interplay of somatostatin, opioid, and GABA neurons in the regulation of the peristaltic reflex," American Journal of Physiology—Gastrointestinal and Liver Physiology, Oct. 1994, 267 (4 Pt 1):G696-G701.

Horvath et al., "New Psychoactive 5H-2,3-Benzodiazepine with a Unique Spectrum of Activity," Arzneimittel-Forschung/Drug Research, Aug. 1989, 39(8):894-899.

International Searh Report and Written Opinion in Application. No. PCT/US2022/014730, dated May 5, 2022, 11 pages.

Kerr et al., "GABA and GABA-receptors in the enteric nervous system," Neuropharmacology, Jul. 1984, 23:835-836.

Krantis et al., "γ-Aminobutyric acid stimulates intrinsic inhibitory and excitatory nerves in the guinea-pig intestine," European Journal of Pharmacology, Oct. 1980, 67(4):461-468.

Krantis, "GABA in the mammalian enteric nervous system," News in Physiological Sciences, Dec. 2000, 15:284-290.

Mennini et al., "Brain Levels of Tofizopam in the Rat and Relationship with Benzodiazepine Receptors," Naunyn Schmiedebergs Archives of Pharmacology, Nov. 1982, 321(2): 112-115.

Ong et al., "Evidence for a physiological role of GABA in the control of guinea-pig intestinal motility," Neuroscience Letters, Sep. 1984, 50:339-343.

Pace et al., "Octatropine methyl bromide and diazepam combination (Valpinax) in patients with irritable bowel syndrome: a multicentre, randomized, placebo-controlled trial," Eur Rev Med Pharmacol Sci, Mar. 2010, 14(3): 155-62.

Pasricha, "Desperately seeking serotonin . . . A commentary on the withdrawal of tegaserod and the state of drug development for functional and motility disorders," Gastroenterology, Jun. 2007, 132(7):2287-2290.

Reis et al., "GABA-induced calcium signaling in cultured enteric neurons is reinforced by activation of cholinergic pathways," Neuroscience, 2006, 139(2):485-494.

Ritchie et al., "Treatment of irritable bowel syndrome with lorazepam, hyoscine butylbromide, and ispaghula husk," Br Med J, Feb. 1979, 1(6160):376-378.

Salari et al., "Systematic review of modulators of benzodiazepine receptors in irritable bowel syndrome: is there hope?" World J Gastroenterol, Oct. 2011, 17(38):4251-7.

Speth et al., "Benzodiazepine binding in human brain: Characterization using [3H] flunitrazepam" Life Sciences, Mar. 1978, 22(10):859-866.

Sullivan et al., "Colonic myoelectrical activity in irritable-bowel syndrome. Effect of eating and anticholinergics," N Engl J Med, Apr. 1978, 20;298(16):878-883.

Talley, "Evaluation of drug treatment in irritable bowel syndrome," British Journal of Clinical Pharmacology, 2003, 56(4):362-369.

Williamson et al., "GABA and nitric oxide synthase immunoreactivities are colocalized in a subset of inhibitory motor neurons of the guinea-pig small intestine," Cell and Tissue Research, Apr. 1996, 284(1):29-37.

Williamson et al., "Transcription and translation of two glutamate decarboxylase genes in the ileum of rat, mouse and guinea pig," Journal of the Autonomic Nervous System, Oct. 1995, 55(1-2):18-28.

* cited by examiner

SUBSTITUTED BENZOPYRAZOLO[1,5-A][1,4]DIAZEPINES AS GABA POSITIVE ALLOSTERIC MODULATORS

CROSS REFERENCE TO RELATED APPLICATION

This application claims the benefit of U.S. Provisional Application No. 63/144,707, filed on Feb. 2, 2021, which is incorporated herein by reference in its entirety.

TECHNICAL FIELD

This disclosure features chemical entities (e.g., a compound or a pharmaceutically acceptable salt thereof, or an N-oxide thereof), which are positive allosteric modulators of one or more GABA-A receptors, e.g., which are peripherally restricted, positive allosteric modulators of one or more GABA-A receptors; e.g., which are positive allosteric modulators of one or more GABA-A receptors and which selectively target the peripheral nervous system and organs of the body, and which do not substantially pass through the blood-brain barrier. Said compounds are useful e.g., for the treatment of systemic diseases of the body, e.g., diseases in which modulation of one or more peripherally restricted GABA-A receptors is beneficial (e.g., diseases or disorders which are mediated by GABA-A neuronal activity, such as, visceral pain, gut motility, irritable bowel syndrome, functional abdominal pain, functional idiopathic diarrhea, inflammatory bowel diseases (e.g., Crohn's disease), drug induced pain, bile salt malabsorption, lactase or other carbohydrate intolerance, interstitial cystitis, chronic pancreatitis, functional dyspepsia, dysmenorrhea, tactile hypersensitivity, tactile dysfunction, somatic pain, asthma, diabetes, anxiety, social impairment, autism spectrum disorder, Rett syndrome, Phelan McDermid syndrome, or Fragile X syndrome). In some embodiments, the chemical entities described herein are useful, e.g., for the treatment of diseases, such as irritable bowel syndrome. This disclosure also features pharmaceutical compositions containing the chemical entities described herein as well as methods for the treatment of systemic diseases of the body (e.g., irritable bowel syndrome), which include administering an effective amount of a chemical entity described herein.

BACKGROUND

Irritable bowel syndrome (IBS) is a disorder that is defined clinically by intermittent abdominal pain in association with altered bowel movements in the absence of any other structural or inflammatory cause. Based on the dominant bowel pattern, IBS patients are clinically phenotyped into three categories: IBS-D (diarrhea predominant), IBS-C (constipation predominant), and IBS-M (mixed or alternating between diarrhea and constipation). IBS is a very common medical disorder with a prevalence estimated between 6-20% in most developed countries and associated with significant impairment of quality of life and socio-economic costs estimated in the billions of dollars every year.[1] Unfortunately, there are few therapeutic options available for patients, with only two approved drugs (lubiprostone and linaclotide) that are both secretagogues and indicated only for symptomatic relief of IBS-C. Currently approved prescription drugs for treatment of IBS-D such as eluxadoline also only provide symptomatic relief with no demonstrated effects on abdominal pain and runs the risk of severe pancreatitis.

The pathogenesis of IBS-D (as with other forms of IBS) remains poorly understood but is thought to be associated with hyperexcitability of neurons, affecting both extrinsic (spinal) and intrinsic (enteric) nerves leading to chronic visceral hypersensitivity and altered motility, respectively. As compared with controls, patients with IBS show increased colonic myoelectrical activity both at baseline and after a meal.[2] Suppression of such excitability is therefore a logical therapeutic target. Most pharmacological approaches to the treatment of IBS focus on the role of serotonin (5-HT), released from chemo- and mechanosensitive enterochromaffin cells residing in the mucosa, leading to activation of nociceptive nerves as well as intrinsic primary afferent neurons (IPANs) in the enteric nervous system (ENS) to initiate reflexes for motility and secretion.[3] Unfortunately, 5-HT receptor modulators (e.g. tegaserod or alosetron) have only been modestly effective and associated with significant adverse effects leading to their withdrawal from the general market. There is therefore a great need for alternative approaches.[4]

Gamma Aminobutyric Acid (GABA) is among the most important inhibitory neurotransmitter in the central nervous system (CNS). Activation of neuronal GABA receptors results in hyperpolarization and stabilization of neuronal excitability. GABA-ergic neurons are also abundant in the enteric nervous system and both GABA-A (inotropic) and GABA-B (metabotropic) receptors are present in the gut, mediating distinct functional effects.[5-13] GABA-B receptor agonists have been investigated for treatment of IBS.[14]

It is thought that the therapeutic benefit of brain penetrating GABA-A modulating benzodiazepines, such as diazepam, in IBS results predominantly from the relief of anxiety that often accompanies IBS.[17] The use of brain penetrating benzodiazepines (or other brain penetrating compounds), however, is clinically problematic both because of sedation, and the potential for addiction and physical dependence on chronic use. An alternate approach has been described for tofisopam and its isomer, dextofisopam which is currently under study for IBS. These molecules have been classified as atypical benzodiazepines which enter the CNS and bind to a novel binding site within the central nervous system that may be responsible for mediating its actions.[18][19]

GABA-A receptor positive allosteric modulators have heretofore been concerned with CNS conditions like anxiety, insomnia, and epilepsy not IBS.

WO 2015/200766 discloses positive allosteric modulators of one or more GABA-A receptors, which selectively target the peripheral nervous system and organs of the body, and which do not substantially pass through the blood-brain barrier.

WO 2020/198275 discloses peripherally-restricted benzodiazepines with reduced blood brain barrier permeability.

SUMMARY

This disclosure features chemical entities (e.g., a compound or a pharmaceutically acceptable salt thereof, or an N-oxide thereof), which are positive allosteric modulators of one or more GABA-A receptors, e.g., which are peripherally restricted, positive allosteric modulators of one or more GABA-A receptors; e.g., which are positive allosteric modulators of one or more GABA-A receptors and which selectively target the peripheral nervous system and organs of the body, and which do not substantially pass through the blood-brain barrier. Said compounds are useful e.g., for the treatment of systemic diseases of the body, e.g., diseases in which modulation of one or more peripherally restricted GABA-A receptors is beneficial (e.g., diseases or disorders which are mediated by GABA-A neuronal activity, such as, visceral pain, gut motility, irritable bowel syndrome (e.g., Crohn's disease), functional abdominal pain, functional idiopathic diarrhea, inflammatory bowel diseases, drug induced pain, bile salt malabsorption, lactase or other carbohydrate intolerance, interstitial cystitis, chronic pancreatitis, functional dyspepsia, dysmenorrhea, tactile hypersensitivity, tactile dysfunction, somatic pain, asthma, diabetes, anxiety, social impairment, autism spectrum disorder, Rett syndrome, Phelan McDermid syndrome, or Fragile X syndrome). In some embodiments, the chemical entities described herein are useful, e.g., for the treatment of diseases, such as irritable bowel syndrome. This disclosure also features pharmaceutical compositions containing the chemical entities described herein as well as methods for the treatment of systemic diseases of the body (e.g., irritable bowel syndrome), which include administering an effective amount of a chemical entity described herein.

In one aspect, this disclosure provides compounds which are GABA-A receptor positive allosteric modulators that are peripherally-restricted to the GABAergic neurons of the body that are present outside of the brain and central nervous system.

Accordingly, provided herein are compounds of Formula (I):

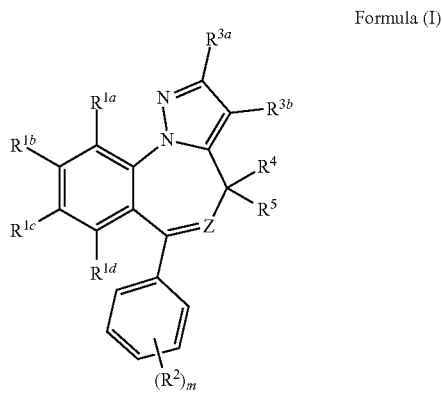

Formula (I)

in which $R^1$, $R^{1b}$, $R^{1c}$, $R^{1d}$, m, $R^2$, $R^{3a}$, $R^{3b}$, $R^4$, $R^5$, and Z can be defined anywhere herein.

In another aspect, this disclosure provides pharmaceutical compositions comprising a compound of Formula (I) as described anywhere herein or a pharmaceutically acceptable salt thereof, and a pharmaceutically acceptable carrier.

In another aspect, this disclosure provides methods and uses of the compounds described herein for positive modulation of GABA-A receptors in tissues and organs outside the brain. In some embodiments, said methods can be carried out in vitro. In some embodiments, said methods can be carried out in vivo. Accordingly, in some embodiments, provided herein is a method of positively modulating GABA-A receptors in tissues and organs outside the brain and central nervous system in a subject in need thereof, the method comprising administering to the subject a therapeutically effective amount of a compound of Formula (I), or a pharmaceutically acceptable salt thereof, or a pharmaceutical composition as described anywhere herein.

In another aspect, this disclosure provides methods for treating or preventing (e.g., treating) visceral pain and modulating gut motility, such as in irritable bowel syndrome (e.g., Crohn's disease), in a subject comprising the administration of a therapeutically effective amount of a peripherally-restricted GABA-A receptor positive allosteric modulator described. Accordingly, in some embodiments, provided herein is a method of treating or preventing (e.g., treating) visceral pain in a subject in need thereof, comprising administering to the subject a therapeutically effective amount of a compound of Formula (I), or a pharmaceutically acceptable salt thereof, or a pharmaceutical composition as described anywhere herein. In some embodiments, provided herein is a method of modulating gut motility in a subject in need thereof, comprising administering to the subject a therapeutically effective amount of a compound of Formula (I), or a pharmaceutically acceptable salt thereof, or a pharmaceutical composition as described anywhere herein.

In another aspect, this disclosure provides a method of treating irritable bowel syndrome in a subject in need thereof, comprising administering to the subject a therapeutically effective amount of a compound of Formula (I), or a pharmaceutically acceptable salt thereof, or a pharmaceutical composition as described anywhere herein.

In another aspect, this disclosure provides a method of treating functional abdominal pain, functional idiopathic diarrhea, inflammatory bowel diseases, drug induced pain, bile salt malabsorption, lactase or other carbohydrate intolerance, interstitial cystitis, chronic pancreatitis, functional dyspepsia, dysmenorrhea, tactile hypersensitivity, tactile dysfunction, somatic pain, asthma, diabetes, anxiety, social impairment, autism spectrum disorder, Rett syndrome, Phelan McDermid syndrome, or Fragile X syndrome in a subject in need thereof, comprising administering to the subject a therapeutically effective amount of a compound of Formula (I), or a pharmaceutically acceptable salt thereof, or a pharmaceutical composition as described anywhere herein.

In another aspect, this disclosure provides methods for suppressing neuronal excitability in tissues and organs outside of the brain and central nervous system, the method comprising administering to a subject in need of such suppressing a therapeutically effective amount of a chemical entity disclosed anywhere herein (e.g., a compound of Formula (I) or a pharmaceutically acceptable salt thereof, or an N-oxide thereof).

In another aspect, this disclosure provides compositions comprising compounds for positive modulation of GABA-A receptors in tissues and organs outside the brain as disclosed herein, and at least one additional therapeutic agent.

In another aspect, this disclosure provides methods and uses of the compositions comprising compounds as disclosed herein, and at least one additional therapeutic agent for positive modulation of GABA-A receptors in tissues and organs outside the brain.

DETAILED DESCRIPTION

This disclosure features chemical entities (e.g., a compound or a pharmaceutically acceptable salt thereof, or an N-oxide thereof), which are positive allosteric modulators of one or more GABA-A receptors, e.g., which are peripherally restricted, positive allosteric modulators of one or more GABA-A receptors; e.g., which are positive allosteric modulators of one or more GABA-A receptors and which selectively target the peripheral nervous system and organs of the body, and which do not substantially pass through the blood-brain barrier. Said compounds are useful e.g., for the treatment of systemic diseases of the body, e.g., diseases in which modulation of one or more peripherally restricted GABA-A receptors is beneficial (e.g., diseases or disorders which are mediated by GABA-A neuronal activity, such as, visceral pain, gut motility, irritable bowel syndrome, functional abdominal pain, functional idiopathic diarrhea, inflammatory bowel diseases (e.g., Crohn's disease), drug induced pain, bile salt malabsorption, lactase or other carbohydrate intolerance, interstitial cystitis, chronic pancreatitis, functional dyspepsia, dysmenorrhea, tactile hypersensitivity, tactile dysfunction, somatic pain, asthma, diabetes, anxiety, social impairment, autism spectrum disorder, Rett syndrome, Phelan McDermid syndrome, or Fragile X syndrome). In some embodiments, the chemical entities described herein are useful, e.g., for the treatment of diseases, such as irritable bowel syndrome. This disclosure also features pharmaceutical compositions containing the chemical entities described herein as well as methods for the treatment of systemic diseases of the body (e.g., irritable bowel syndrome), which include administering an effective amount of a chemical entity described herein.

The disclosure summarized above may be better understood by referring to the following description. This description of one or more embodiments, set out below to enable one to practice an implementation of this disclosure, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of this disclosure. Those skilled in the art should also realize that such equivalent assemblies do not depart from the spirit and scope of this disclosure in its broadest form.

Overview

In one aspect, this disclosure provides methods for treatment of visceral pain and modulating gut motility in a subject, such as that caused by IBS, by positively modulating the GABA-A receptor in the enteric nervous system without the usual CNS side effects of GABA modulation is provided. It is contemplated that the methods described herein are effective in treating visceral pain caused by other ailments, not only IBS. Examples of non-IBS related ailments which can be treated by the inventive methods, include functional abdominal pain, functional idiopathic diarrhea, inflammatory bowel diseases such as Crohn's disease, drug induced pain, bile salt malabsorption, lactase or other carbohydrate intolerance, interstitial cystitis, chronic pancreatitis, functional dyspepsia, dysmenorrhea, tactile hypersensitivity, somatic pain, asthma, and diabetes.

In another aspect, this disclosure provides methods for the treatment of tactile dysfunction, anxiety, or social impairment in a subject in need thereof, the method comprising administering to the subject a chemical entity disclosed anywhere herein (e.g., a compound of Formula (I) or a pharmaceutically acceptable salt thereof, or an N-oxide thereof). In some embodiments, the subject is diagnosed with Autism Spectrum Disorder, Rett syndrome, Phelan McDermid syndrome, or Fragile X syndrome.

In another aspect, this disclosure provides methods for suppressing neuronal excitability in tissues and organs outside of the brain and central nervous system, the method comprising administering to a subject in need of such suppressing a therapeutically effective amount of a peripherally-restricted GABA-A receptor positive allosteric modulator, wherein the peripherally-restricted GABA-A receptor positive allosteric modulator is a chemical entity disclosed anywhere herein (e.g., a compound of Formula (I) or a pharmaceutically acceptable salt thereof, or an N-oxide thereof). In some embodiments, neuronal excitability is GABAergic neuronal excitability in tissues and organs outside of the brain and central nervous system. In some embodiments, suppressing neuronal excitability in tissues and organs outside of the brain and central nervous system comprises positively modulating GABA-A receptors in tissues and organs outside the brain and central nervous system. In some embodiments, the peripherally-restricted GABA-A receptor positive allosteric modulator does not substantially cross an intact blood brain barrier of the subject. In some embodiments, less than 50% (e.g., less than 40%, less than 30%, less than 20%, less than 10%, less than 5%, less than 1%, less than 0.5%, or less than 0.1%) of the peripherally-restricted GABA-A receptor positive allosteric modulator crosses an intact blood brain barrier of the subject. In certain embodiments, less than 5% of the peripherally-restricted GABA-A receptor positive allosteric modulator crosses an intact blood brain barrier of the subject. In certain embodiments, less than 1% (e.g., less than 0.5% or less than 0.1%) of the peripherally-restricted GABA-A receptor positive allosteric modulator crosses an intact blood brain barrier of the subject. In some embodiments, the ratio of a concentration of the peripherally-restricted GABA-A receptor positive allosteric modulator in the brain to a concentration of the peripherally-restricted GABA-A receptor positive allosteric modulator in the circulating plasma is about 1:5. In some embodiments, the ratio of a concentration of the peripherally-restricted GABA-A receptor positive allosteric modulator in the brain to a concentration of the peripherally-restricted GABA-A receptor positive allosteric modulator in the circulating plasma is about 1:10. In some embodiments, the average concentration of the peripherally-restricted GABA-A receptor positive allosteric modulator in the brain is less than 62.5 nM. In some embodiments, the peripherally-restricted GABA-A receptor positive allosteric modulator binds to the GABA-A receptor with a Ki of less than 500 nM. In some embodiments, upon administration of the peripherally-restricted GABA-A receptor positive allosteric modulator the subject does not experience unwanted sedation side effects. In some embodiments, the peripherally-restricted GABA-A receptor positive allosteric modulator is a pharmaceutically acceptable salt of the compound of Formula (I) (e.g., a pharmaceutically acceptable salt of a compound delineated in Table C1). In some embodiments, the peripherally-restricted GABA-A receptor positive allosteric modulator is a compound of Formula (I). For example, the peripherally-restricted GABA-A receptor positive allosteric modulator can be a compound delineated in Table C1. In some embodiments, the method further comprises administering the peripherally-restricted GABA-A receptor positive allosteric modulator as a pharmaceutical composition comprising the peripherally-restricted GABA-A receptor positive allosteric modulator and a pharmaceutically acceptable carrier. In some embodiments, the method further comprises administering at least one additional therapeutic agent. In some embodiments, the method further comprises administering at least one additional therapeutic agent for positive modulation of GABA-A receptors in tissues and organs outside the brain.

Through modulation of physical properties such as membrane permeability and incorporation of functional groups known to enhance recognition by blood-brain barrier transporters, GABA-A receptor positive allosteric modulators used in this disclosure, are restricted from the CNS so they do not produce unwanted side effects such as sedation yet still exert beneficial pharmacological effects on the enteric nervous system.

Pharmacological access to the CNS is restricted by the blood brain barrier (BBB), a system that includes tight junctions between vascular endothelial cells and membrane transporters which work to minimize brain exposure of many circulating biomolecules, peptides, and drugs. Several therapeutically useful drugs take advantage of this restriction to provide a peripheral benefit without CNS complications, such as the well-known non-sedating antihistamines loratadine and cetirizine.[20] Since all of the known GABA-A positive allosteric modulators, such as diazepam and midazolam, were designed to treat CNS disorders; non-brain-penetrating analogs have not been generally described, or only described as intermediates toward more useful compounds.

This disclosure provides, inter alia, chemical compounds according to Formula (I), and pharmaceutically acceptable salts, solvates, and stereoisomers thereof, or any prodrug equivalents (such as esters) thereof, wherein one of the $R^3$ and $R^{3a}$ groups contain a functional group that reduces blood-brain barrier permeability, as shown below.

Accordingly, in one aspect, this disclosure features compounds of Formula (I):

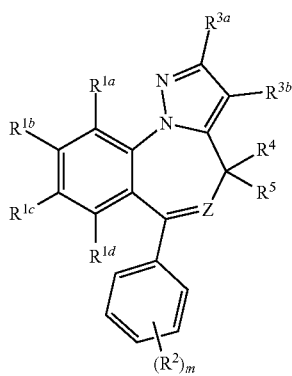

Formula (I)

or a pharmaceutically acceptable salt thereof, wherein:
$R^{1a}$, $R^{1b}$, $R^{1c}$, and $R^{1d}$ are each independently selected from the group consisting of: H, halo, $C_{1-6}$ alkyl, $C_{1-6}$ haloalkyl, $C_{2-6}$ alkenyl, $C_{2-6}$ alkynyl, nitro, cyano, $C_{1-6}$ alkoxy, $C_{1-6}$ haloalkoxy, $C_{1-6}$ thioalkoxy, $C_{1-6}$ halothioalkoxy, $S(O)_2(C_{1-6}$ alkyl), $S(=O)(=NH)C_{1-6}$ alkyl, $Si(C_{1-6}$ alkyl)$_3$, $C_{3-6}$ cycloalkyl, $C_{6-10}$ aryl, $NR^6R^7$, $C(O)R^6$, and $C(O)NR^6R^7$,
wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl;
each occurrence of $R^2$ is independently selected from the group consisting of: halo, $C_{1-6}$ alkyl, $C_{1-6}$ haloalkyl, $C_{2-6}$ alkenyl, $C_{2-6}$ alkynyl, $NO_2$, cyano, $C_{1-6}$ alkoxy, $C_{1-6}$ haloalkoxy, $SO_2(C_{1-6}$ alkyl), $S(=O)(=NH)C_{1-6}$ alkyl, $C_{3-6}$ cycloalkyl, $NR^6R^7$, $C(O)R^6$, and $C(O)NR^6R^7$;
m is 0, 1, 2, 3, 4, or 5;
one of $R^{3a}$ and $R^{3b}$ is X, and the other of $R^{3a}$ and $R^{3b}$ is $R^3$;

X is selected from the group consisting of: —$CO_2H$, —$CH(R^X)CO_2H$, —$C(O)Y$, —$CH(R^X)C(O)Y$, —$S(O)_2Y$, —$CH(R^X)S(O)_2Y$, —$(C_{1-3}$ alkylene)-$N^+(C_{1-3}$ alkyl)$_3$, —$P(=O)(OH)_2$, —$SO_3H$

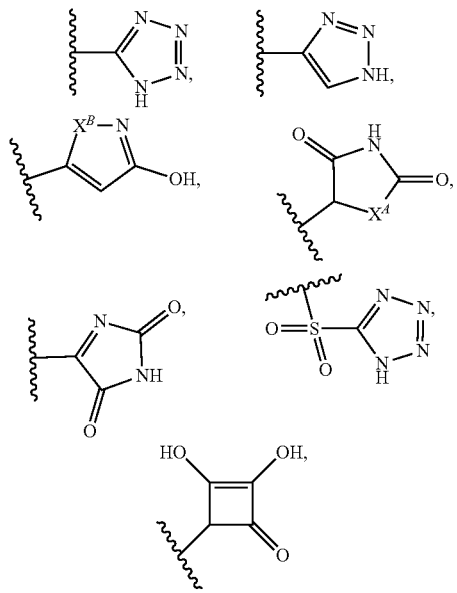

and C(O)glucuronic acid;
$X^A$ and $X^B$ are independently O, S, N(H), or N($C_{1-3}$ alkyl);
$R^X$ is selected from the group consisting of: H, $C_{1-6}$ alkyl, —OH, and —$NR^6R^7$;
Y is selected from the group consisting of:
(i) —$NR^6R^7$;
(ii) —$NR^8$—$CH_2CH_2O$—(—$CH_2CH_2O$—)$_n$—$Y^4$, wherein n is an integer between 0 and 20; and
(iii) —NR—$Y^2$—$Y^3$;
$Y^2$ is $C_{2-6}$ alkylene;
$Y^3$ is selected from the group consisting of: —$NR^6R^7$; —$NR^9S(O)_2NR^9R^{10}$; —$S(O)_2R^6$; —$S(=O)R^6$(=$NR^8$); and —$P(=O)(C_{1-3}$ alkyl)$_2$;
$Y^4$ is H or $C_{1-6}$ alkyl;
$R^3$ is selected from the group consisting of:
H, halo, or cyano;
$C_{1-6}$ alkyl, $C_{1-6}$ haloalkyl, $C_{2-6}$ alkenyl, or $C_{2-6}$ alkynyl;
$C_{1-6}$ alkoxy or $C_{1-6}$ haloalkoxy;
—$NR^6R^7$, —$C(O)NR^6R^7$, or —$CH_2NR^6R^7$;
$C_{3-6}$ cycloalkyl;
$C_{6-10}$ aryl; and
heteroaryl including from 5-6 ring atoms, wherein from 1-4 ring atoms are heteroatoms each independently selected from the group consisting of: N, N($R^1$), O, and S;
$R^4$ and $R^5$ are independently selected from the group consisting of: H, $C_{1-6}$ alkyl, —OH, and —$NR^6R^7$; or
$R^4$ and $R^5$ taken together with the carbon atom to which each is attached forms a $C_{3-6}$ cycloalkyl;
each occurrence of $R^6$ and $R^7$ is independently selected from the group consisting of: H, $C_{1-6}$ alkyl, $C_{1-6}$ haloalkyl, $C_{3-6}$ cycloalkyl, phenyl, —($C_{1}$-4 alkylene)-phenyl, $C(=O)R^9$, $C(=O)OR^9$, and $C(=O)NR^9R^{10}$; or
a pair of $R^6$ and $R^7$ on the same nitrogen atom, taken together with said nitrogen atom connecting them, forms a saturated, partially unsaturated, or aromatic ring including 4-8 ring atoms, wherein from 0-2 ring atoms (in addition to the nitrogen atom connecting $R^6$ and $R^7$) are ring heteroatoms each independently selected from the group consisting of: N, N($R^8$), O, and S;

each occurrence of $R^8$ is independently selected from the group consisting of: H, $C_{1-6}$ alkyl, —C(=O)$R^9$, —C(=O)O$R^9$, and —C(=O)N$R^9R^{10}$;

each occurrence of $R^9$ and $R^{10}$ is H or $C_{1-6}$ alkyl; and

Z is N or

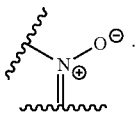 [SMILES: *[N+](=*)[O-]]

In some embodiments, $R^{3a}$ is X; and $R^{3b}$ is $R^3$.

In some embodiments, $R^{3a}$ is $R^3$; and $R^{3b}$ is X.

In some embodiments, from 1-2 of $R^{1a}$, $R^{1b}$, $R^{1c}$, and $R^{1d}$ is an independently selected substituent other than H.

In certain of these embodiments, one of $R^{1a}$, $R^{1b}$, $R^{1c}$, and $R^{1d}$ (e.g., $R^{1c}$ or $R^{1d}$ (e.g., $R^{1c}$)) is selected from the group consisting of: halo, $C_{1-6}$ alkyl, $C_{1-6}$ haloalkyl, $C_{2-6}$ alkenyl, $C_{2-6}$ alkynyl, nitro, cyano, $C_{1-6}$ alkoxy, $C_{1-6}$ haloalkoxy, $C_{1-6}$ thioalkoxy, $C_{1-6}$ halothioalkoxy, S(O)$_2$($C_{1-6}$ alkyl), S(=O)(=NH)$C_{1-6}$ alkyl, Si($C_{1-6}$ alkyl)$_3$, $C_{3-6}$ cycloalkyl, $C_{6-10}$ aryl, N$R^6R^7$, C(O)$R^6$, and C(O)N$R^6R^7$, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl; and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is selected from the group consisting of: halo, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ thioalkoxy, $C_{1-6}$ halothioalkoxy, S(O)$_2$($C_{1-6}$ alkyl), S(=O)(=NH)$C_{1-6}$ alkyl, Si($C_{1-6}$ alkyl)$_3$, $C_{3-6}$ cycloalkyl, and $C_{6-10}$ aryl, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl; and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is halo (e.g., —Cl or —Br (e.g., —Cl)); and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is $C_{1-6}$ alkyl (e.g., —$C_{1-3}$ alkyl (e.g., methyl)); and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is $C_{1-6}$ haloalkyl (e.g., —$C_{1-3}$ haloalkyl (e.g., —CF$_3$)); and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is $C_{2-6}$ alkynyl (e.g., );

and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is $C_{1-6}$ alkoxy (e.g., $C_{1-3}$ alkoxy, such as methoxy), $C_{1-6}$ haloalkoxy (e.g., $C_{1-3}$ haloalkoxy, such as —OCF$_3$), $C_{1-6}$ thioalkoxy (e.g., $C_{1-3}$ thioalkoxy, such as —SCH$_3$), or $C_{1-6}$ halothioalkoxy (e.g., $C_{1-3}$ halothioalkoxy (e.g., —SCF$_3$); and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is Si($C_{1-6}$ alkyl)$_3$ (e.g., SiMe$_3$); and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is S(O)$_2$($C_{1-6}$ alkyl) (e.g., S(O)$_2$CH$_3$) or S(=O)(=NH)$C_{1-6}$ alkyl; and the other three of $R^{1a}$, $R^{1b}$, $R^{1c}$, and $R^{1d}$ are H.

In certain embodiments, one of $R^{1a}$, $R^{1b}$, $R^{1c}$, and $R^{1d}$ (e.g., $R^{1c}$ or $R^{1d}$ (e.g., $R^{1c}$)) is $C_{3-6}$ cycloalkyl (e.g., cyclopropyl) or $C_{6-10}$ aryl (e.g., phenyl), wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl; and the other three of $R^{1a}$, $R^{1b}$, $R^{1c}$, and $R^{1d}$ are H.

In certain embodiments, $R^{1c}$ is selected from the group consisting of: halo, $C_{1-6}$ alkyl, $C_{1-6}$ haloalkyl, $C_{2-6}$ alkenyl, $C_{2-6}$ alkynyl, nitro, cyano, $C_{1-6}$ alkoxy, $C_{1-6}$ haloalkoxy, $C_{1-6}$ thioalkoxy, $C_{1-6}$ halothioalkoxy, S(O)$_2$($C_{1-6}$ alkyl), S(=O)(=NH)$C_{1-6}$ alkyl, Si($C_{1-6}$ alkyl)$_3$, $C_{3-6}$ cycloalkyl, $C_{6-10}$ aryl, N$R^6R^7$, C(O)$R^6$, and C(O)N$R^6R^7$, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl; and $R^{1a}$, $R^{1b}$, and $R^{1d}$ are H.

In certain of these embodiments, $R^{1c}$ is selected from the group consisting of: halo, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ thioalkoxy, $C_{1-6}$ halothioalkoxy, S(O)$_2$($C_{1-6}$ alkyl), S(=O)(=NH)$C_{1-6}$ alkyl, Si($C_{1-6}$ alkyl)$_3$, $C_{3-6}$ cycloalkyl, $C_{6-10}$ aryl, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl; and $R^{1a}$, $R^{1b}$, and $R^{1d}$ are H.

In certain of the foregoing embodiments, $R^{1c}$ is halo (e.g., —Cl or —Br (e.g., —Cl)); and $R^{1a}$, $R^{1b}$, and $R^{1d}$ are H.

In certain embodiments, $R^{1c}$ is $C_{1-6}$ alkyl (e.g., —$C_{1-3}$ alkyl (e.g., methyl)); and $R^{1a}$, $R^{1b}$, and $R^{1d}$ are H.

In certain embodiments, $R^{1c}$ is $C_{1-6}$ haloalkyl (e.g., —$C_{1-3}$ haloalkyl (e.g., —CF$_3$); and $R^{1a}$, $R^{1b}$, and $R^{1d}$ are H.

In certain embodiments, $R^{1c}$ is $C_{2-6}$ alkynyl (e.g., 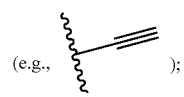);

and $R^{1a}$, $R^{1b}$, and $R^{1d}$ are H.

In certain embodiments, $R^{1c}$ is $C_{1-6}$ alkoxy (e.g., $C_{1-3}$ alkoxy, such as methoxy), $C_{1-6}$ haloalkoxy (e.g., $C_{1-3}$ haloalkoxy, such as —OCF$_3$), $C_{1-6}$ thioalkoxy (e.g., $C_{1-3}$ thioalkoxy, such as —SCH$_3$), or $C_{1-6}$ halothioalkoxy (e.g., $C_{1-3}$ halothioalkoxy (e.g., —SCF$_3$); and $R^{1a}$, $R^{1b}$, and $R^{1d}$ are H.

In certain embodiments, $R^{1c}$ is Si($C_{1-6}$ alkyl)$_3$ (e.g., SiMe$_3$); and $R^{1a}$, $R^{1b}$, and $R^{1d}$ are H.

In certain embodiments, $R^{1c}$ is S(O)$_2$($C_{1-6}$ alkyl) (e.g., S(O)$_2$CH$_3$) or S(=O)(=NH)$C_{1-6}$ alkyl; and $R^{1a}$, $R^{1b}$, and $R^{1d}$ are H.

In certain embodiments, $R^{1c}$ is $C_{3-6}$ cycloalkyl (e.g., cyclopropyl) or $C_{6-10}$ aryl (e.g., phenyl), wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl; and $R^{1a}$, $R^{1b}$, and $R^{1d}$ are H.

In some embodiments, each of $R^{1a}$, $R^{1b}$, $R^{1c}$, and $R^{1d}$ is H.

In some embodiments, m is 1 or 2. In certain of these embodiments, m is 1.

In certain embodiments,

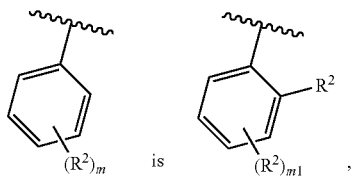

wherein m1 is 0 or 1. In certain of these embodiments, m1 is 0. In other embodiments, m1 is 1.

In certain embodiments,

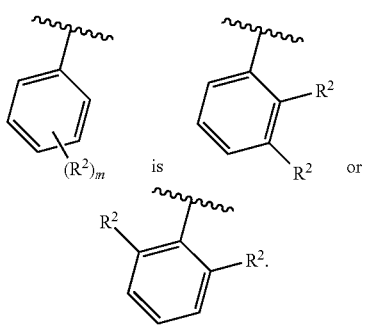

In some embodiments, each $R^2$ is independently selected from the group consisting of: halo, $C_{1-6}$ alkyl, $C_{1-6}$ haloalkyl, $C_{2-6}$ alkenyl, $C_{2-6}$ alkynyl, $NO_2$, cyano, $C_{1-6}$ alkoxy, $C_{1-6}$ haloalkoxy, $SO_2(C_{1-6}$ alkyl), and $C_{3-6}$ cycloalkyl.

In certain of these embodiments, each $R^2$ is independently selected from the group consisting of: halo, $C_{1-6}$ alkyl, $C_{1-6}$ haloalkyl, cyano, $C_{1-6}$ alkoxy, and $C_{1-6}$ haloalkoxy.

As non-limiting examples of the foregoing embodiments, each $R^2$ can be an independently selected halo, such as —F, —Cl, or —Br.

In some embodiments, each of $R^4$ and $R^5$ is H.

In some embodiments, one of $R^4$ and $R^5$ is $C_{1-6}$ alkyl; and the other of $R^4$ and $R^5$ is H.

In some embodiments, one of $R^4$ and $R^5$ is —OH; and the other of $R^4$ and $R^5$ is H.

In some embodiments, X is —$CO_2H$ or —$CH(R^X)CO_2H$. In certain of these embodiments, X is —$CO_2H$.

In some embodiments, X is —C(O)Y or —$CH(R^X)C(O)$Y. In certain of these embodiments, X is —C(O)Y.

In certain embodiments (when X is —C(O)Y or —CH($R^X$)C(O)Y (e.g., —C(O)Y)), Y is —$NR^6R^7$. For example, Y can be $NH_2$, $NH(C_{1-3}$ alkyl), or $N(C_{1-3}$ alkyl)$_2$.

In certain embodiments (when X is —C(O)Y or —CH($R^X$)C(O)Y (e.g., —C(O)Y)), Y is —$NR^8$—$Y^2$—$Y^3$. In certain of these embodiments, Y is —N(H)—$Y^2$—$Y^3$.

In certain of the foregoing embodiments, $Y^2$ is straight-chain $C_{2-4}$ alkylene. For example, $Y^2$ can be —$CH_2CH_2$— or —$CH_2CH_2CH_2$—.

In certain embodiments, $Y^3$ is $NR^6R^7$ (e.g., NHC(=O)$NR^9R^{10}$). For example, $Y^3$ can be NHC(=O)$NH_2$.

In certain embodiments, $Y^3$ is —NR'S(O)$_2NR^9R^{10}$. For example, $Y^3$ can be —NHS(O)$_2NH_2$.

In some embodiments, $R^3$ is H.

In some embodiments, $R^3$ is halo. For example, $R^3$ can be —Cl or —Br.

In some embodiments, $R^3$ is $C_{1-6}$ alkyl or $C_{1-6}$ haloalkyl. For example, $R^3$ can be $C_1$-3 alkyl (e.g., methyl).

In some embodiments, Z is N.

In some embodiments, Z is

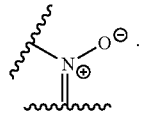

Non-Limiting Combination [AA]:
In certain embodiments:
one of $R^{1a}$, $R^{1b}$, $R^{1c}$, and $R^{1d}$ is selected from the group consisting of: halo, $C_{1-6}$ alkyl, $C_{1-6}$ haloalkyl, $C_{2-6}$ alkenyl, $C_{2-6}$ alkynyl, nitro, cyano, $C_{1-6}$ alkoxy, $C_{1-6}$ haloalkoxy, $C_{1-6}$ thioalkoxy, $C_{1-6}$ halothioalkoxy, $S(O)_2(C_{1-6}$ alkyl), $S(=O)(=NH)C_{1-6}$ alkyl, $Si(C_{1-6}$ alkyl)$_3$, $C_{3-6}$ cycloalkyl, $C_{6-10}$ aryl, $NR^6R^7$, $C(O)R^6$, and $C(O)NR^6R^7$, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl;
the other three of $R^{1a}$, $R^{1b}$, $R^{1c}$, and $R^{1d}$ are H;
m is 1 or 2;
each $R^2$ is independently selected from the group consisting of: halo, $C_{1-6}$ alkyl, $C_{1-6}$ haloalkyl, $C_{2-6}$ alkenyl, $C_{2-6}$ alkynyl, $NO_2$, cyano, $C_{1-6}$ alkoxy, $C_{1-6}$ haloalkoxy, $SO_2(C_{1-6}$ alkyl), and $C_{3-6}$ cycloalkyl;
$R^{3a}$ is X; and
$R^{3b}$ is $R^3$.

In certain embodiments of [AA], $R^{1c}$ is selected from the group consisting of: halo, $C_{1-6}$ alkyl, $C_{1-6}$ haloalkyl, $C_{2-6}$ alkenyl, $C_{2-6}$ alkynyl, nitro, cyano, $C_{1-6}$ alkoxy, $C_{1-6}$ haloalkoxy, $C_{1-6}$ thioalkoxy, $C_{1-6}$ halothioalkoxy, $S(O)_2(C_{1-6}$ alkyl), $S(=O)(=NH)C_{1-6}$ alkyl, $Si(C_{1-6}$ alkyl)$_3$, $C_{3-6}$ cycloalkyl, $C_{6-10}$ aryl, $NR^6R^7$, $C(O)R^6$, and $C(O)NR^6R^7$, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl.

Non-Limiting Combination [BB]:
one of $R^{1a}$, $R^{1b}$, $R^{1c}$, and $R^{1d}$ is selected from the group consisting of: halo, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ thioalkoxy, $C_{1-6}$ halothioalkoxy, $S(O)_2(C_{1-6}$ alkyl), $S(=O)(=NH)C_{1-6}$ alkyl, $Si(C_{1-6}$ alkyl)$_3$, $C_{3-6}$ cycloalkyl, and $C_{6-10}$ aryl, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl;
the other three of $R^{1a}$, $R^{1b}$, $R^{1c}$, and $R^{1d}$ are H;
m is 1 or 2;
each $R^2$ is independently selected from the group consisting of: halo, $C_{1-6}$ alkyl, $C_{1-6}$ haloalkyl, cyano, $C_{1-6}$ alkoxy, and $C_{1-6}$ haloalkoxy;
$R^{3a}$ is X; and
$R^{3b}$ is $R^3$.

In certain embodiments, of [BB], $R^{1c}$ is selected from the group consisting of: halo, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ thioalkoxy, $C_{1-6}$ halothioalkoxy, $S(O)_2(C_{1-6}$ alkyl), $S(=O)(=NH)C_{1-6}$ alkyl, $Si(C_{1-6}$ alkyl)$_3$, $C_{3-6}$ cycloalkyl, and $C_{6-10}$ aryl, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl.

Non-Limiting Combination [CC]:
one of $R^{1a}$, $R^{1b}$, $R^{1c}$, and $R^{1d}$ is halo (e.g., —Cl);
the other three of $R^{1a}$, $R^{1b}$, $R^{1c}$, and $R^{1d}$ are H;
m is 1 or 2;
each $R^2$ is an independently selected halo, such as —F, —Cl, or —Br;
$R^{3a}$ is X; and
$R^{3b}$ is $R^3$.

In certain embodiments of [CC], $R^{1c}$ is halo (e.g., —Cl).
In certain embodiments of [AA], [BB], or [CC]

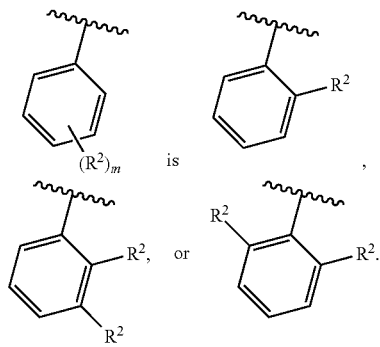

is

In certain embodiments of [AA], [BB], or [CC], $R^3$ is H.
In certain embodiments of [AA], [BB], or [CC], $R^3$ is halo or $C_{1-3}$ alkyl.
In certain embodiments of [AA], [BB], or [CC], $R^4$ and $R^5$ are each H.
In certain embodiments of [AA], [BB], or [CC], X is —CO$_2$H.
In certain embodiments of [AA], [BB], or [CC], X is —C(O)N(H)—Y$^2$—Y$^3$ (e.g., —C(O)N(H)CH$_2$CH$_2$—Y$^3$). In certain of these embodiments, Y$^3$ is NR$^6$R$^7$ (e.g., NHC(=O)NR$^9$R$^{10}$). For example, Y$^3$ can be NHC(=O)NH$_2$. In certain embodiments, Y$^3$ is —NR$^9$S(O)$_2$NR$^9$R$^{10}$. For example, Y$^3$ can be —NHS(O)$_2$NH$_2$.
In certain embodiments of [AA], [BB], or [CC], Z is N.

In certain embodiments, the compound of Formula (I) is a compound of Formula (Ia):

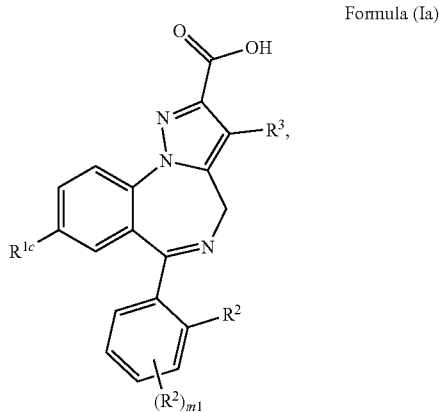

Formula (Ia)

or a pharmaceutically acceptable salt thereof, wherein:
$R^{1c}$ is selected from the group consisting of: halo, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ thioalkoxy, $C_{1-6}$ halothioalkoxy, $S(O)_2(C_{1-6}$ alkyl), $S(=O)(=NH)C_{1-6}$ alkyl, $Si(C_{1-6}$ alkyl)$_3$, $C_{3-6}$ cycloalkyl, and $C_{6-10}$ aryl, wherein the $C_{3-6}$ cycloalkyl and $C_{6-10}$ aryl are each optionally substituted with from 1-4 substituents each independently selected from the group consisting of: halo, cyano, $C_{1-6}$ alkyl, and $C_{1-6}$ haloalkyl;
m1 is 0 or 1;
each $R^2$ is independently selected from the group consisting of: halo, $C_{1-6}$ alkyl, $C_{1-6}$ haloalkyl, $C_{2-6}$ alkenyl, $C_{2-6}$ alkynyl, NO$_2$, cyano, $C_{1-6}$ alkoxy, $C_{1-6}$ haloalkoxy, SO$_2$(C$_{1-6}$ alkyl), and $C_{3-6}$ cycloalkyl; and
$R^3$ is H, halo, or $C_{1-3}$ alkyl.

In certain embodiments of Formula (Ia), $R^{1c}$ is halo (e.g., —Cl or —Br).
In certain embodiments of Formula (Ia), $R^3$ is H.
In certain embodiments of Formula (Ia), $R^3$ is halo.
In certain embodiments of Formula (Ia), m1 is 0.
In certain embodiments of Formula (Ia), m1 is 1.
In certain embodiments of Formula (Ia), each $R^2$ is an independently selected halo (e.g., —F or —Cl (e.g., —F)).
In certain embodiments, the compound is selected from the group consisting of the compounds in Table C1, or a pharmaceutically acceptable salt thereof.

TABLE C1

| Compound # | Example # | Structure |
|---|---|---|
| 101 | 1 | 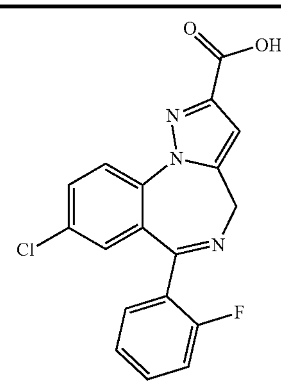 |

TABLE C1-continued

| Compound # | Example # | Structure |
|---|---|---|
| 102 | 2 | (structure: 8-ethynyl, 6-(2-fluorophenyl) pyrazolo-benzodiazepine-2-carboxylic acid) |
| 103 | 3 | (structure: 8-cyclopropyl, 6-(2-fluorophenyl) pyrazolo-benzodiazepine-2-carboxylic acid) |
| 104 | 4 | (structure: 8-methyl, 6-(2-fluorophenyl) pyrazolo-benzodiazepine-2-carboxylic acid) |
| 105 | 5 | (structure: 6-(2-fluorophenyl) pyrazolo-benzodiazepine-2-carboxylic acid) |

TABLE C1-continued
| Compound # | Example # | Structure |
|---|---|---|
| 106 | 6 | 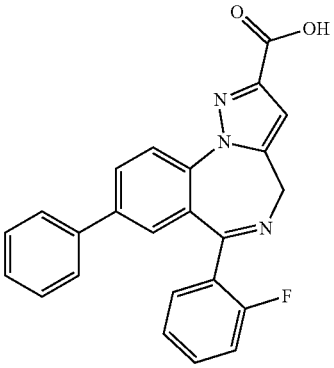 |
| 107 | 7 | 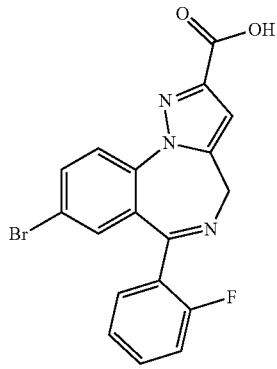 [SMILES: O=C(O)c1cc2n(n1)-c1ccc(Cl)cc1C(c1ccccc1F)=NC2] |
| 108 | 8 | 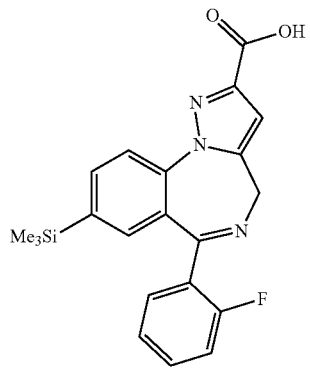 [SMILES: C[Si](C)(C)c1ccc2c(c1)C(c1ccccc1F)=NCc1cc(C(=O)O)nn1-2] |
| 109 | 9 | 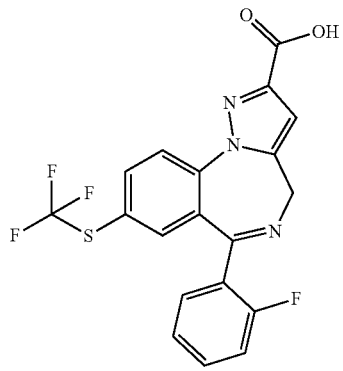 [SMILES: O=C(O)c1cc2n(n1)-c1ccc(SC(F)(F)F)cc1C(c1ccccc1F)=NC2] |

TABLE C1-continued

| Compound # | Example # | Structure |
|---|---|---|
| 110 | 10 | (structure: pyrazolo-benzodiazepine with CF₃ on benzo ring, 2-fluorophenyl, carboxylic acid) |
| 111 | 11 | (structure: pyrazolo-benzodiazepine with OCF₃ on benzo ring, 2-fluorophenyl, carboxylic acid) |
| 112 | 12 | (structure: pyrazolo-benzodiazepine with Cl on benzo ring, 2-fluorophenyl, carboxylic acid) |
| 113 | 13 | (structure: pyrazolo-benzodiazepine with Cl on benzo ring, 2-bromophenyl, carboxylic acid) |

TABLE C1-continued

| Compound # | Example # | Structure |
|---|---|---|
| 114 | 14 | 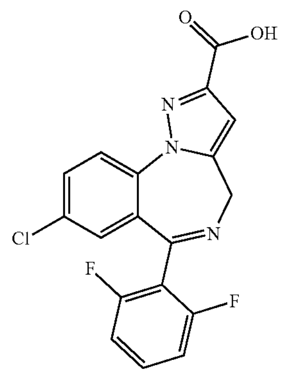 [SMILES: O=C(O)c1cc2n(n1)-c1ccc(Cl)cc1C(c1c(F)cccc1F)=NC2] |
| 115 | 15 | 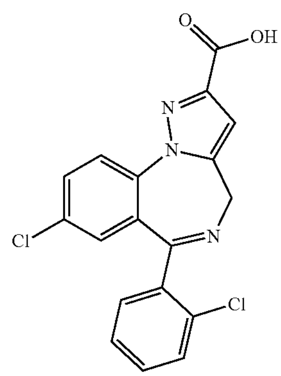 [SMILES: O=C(O)c1cc2n(n1)-c1ccc(Cl)cc1C(c1ccccc1Cl)=NC2] |
| 116 | 16 | 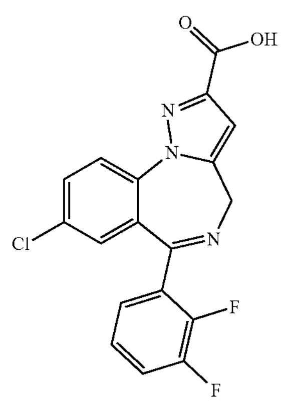 [SMILES: O=C(O)c1cc2n(n1)-c1ccc(Cl)cc1C(c1cccc(F)c1F)=NC2] |
| 117 | 17 | 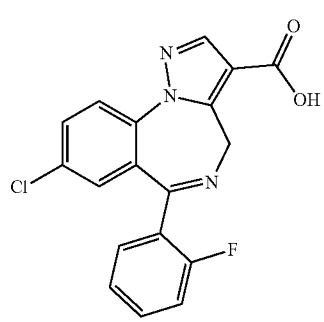 [SMILES: O=C(O)c1cnn2c1CN=C(c1ccccc1F)c1cc(Cl)ccc1-2] |

TABLE C1-continued

| Compound # | Example # | Structure |
|---|---|---|
| 118 | 18 | 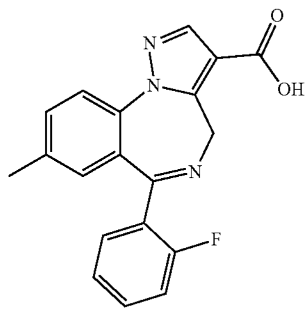 [SMILES: Cc1ccc2c(c1)C(c1ccccc1F)=NCc1c(C(=O)O)cnn1-2] |
| 119 | 19 | 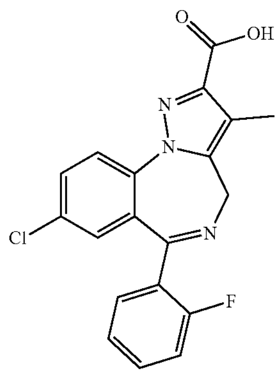 [SMILES: Cc1c(C(=O)O)nn2c1CN=C(c1ccccc1F)c1cc(Cl)ccc1-2] |
| 120 | 20 | 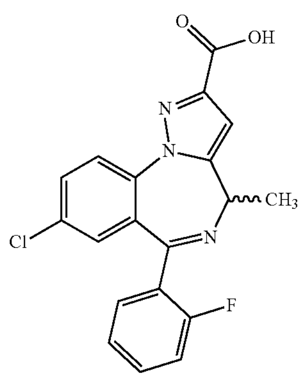 [SMILES: CC1N=C(c2ccccc2F)c2cc(Cl)ccc2-n2nc(C(=O)O)cc21] |
| 121 | 21 | 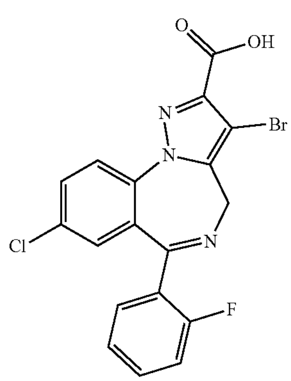 [SMILES: O=C(O)c1nn2c(c1Br)CN=C(c1ccccc1F)c1cc(Cl)ccc1-2] |

TABLE C1-continued

| Compound # | Example # | Structure |
|---|---|---|
| 122 | 22 | (structure) |
| 123 | 23 | (structure) |
| 124 | 24 | (structure) |
| 125 | 25 | (structure) |

TABLE C1-continued
| Compound # | Example # | Structure |
|---|---|---|
| 126 | 26 | 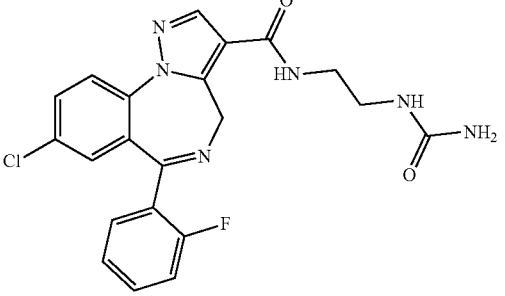 |
| 127 | 27 | 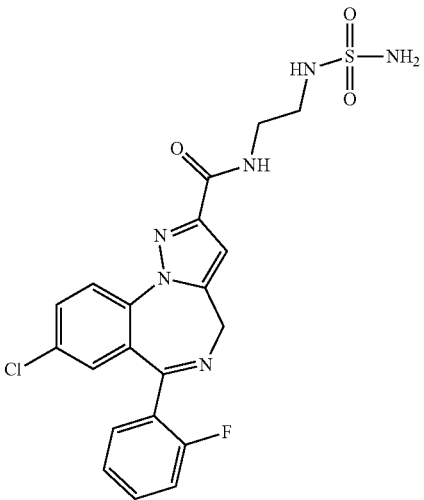 [SMILES: NS(=O)(=O)NCCNC(=O)c1cc2n(n1)-c1ccc(Cl)cc1C(c1ccccc1F)=NC2] |
| 128 | 28 | 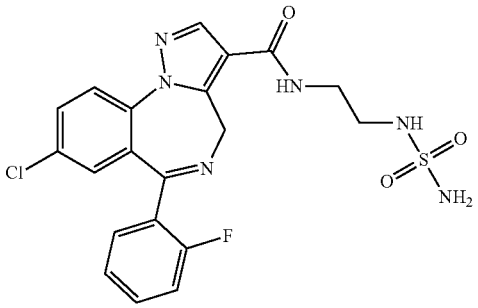 [SMILES: NS(=O)(=O)NCCNC(=O)c1cnn2c1CN=C(c1ccccc1F)c1cc(Cl)ccc1-2] |
| 129 | 29 | 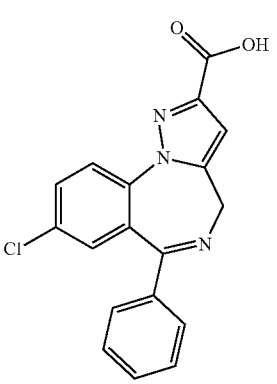 [SMILES: O=C(O)c1cc2n(n1)-c1ccc(Cl)cc1C(c1ccccc1)=NC2] |

In another aspect, this disclosure provides pharmaceutical compositions comprising the compounds of Formula (I), as described herein, and a pharmaceutically acceptable carrier.

In a further aspect, this disclosure provides a salt (e.g., a pharmaceutically acceptable salt) of the Formula (I) compounds described herein.

Definitions

As used herein, the chemical terms used above are standard chemical terminology. Sample definitions of such chemical substituents can be found in U.S. Pat. No. 8,530,438; which is incorporated herein by reference in its entirety.

As used herein, "peripherally restricted" or "restricted access to the central nervous system" generally refers to a chemical entity (e.g., a compound or a pharmaceutically acceptable thereof) that does not substantially cross an intact blood brain barrier of a subject. The term also encompasses compounds that may cross an intact blood brain barrier, but upon administration is rapidly metabolized to a form that does not substantially cross an intact blood brain barrier of the subject. A compound may be considered "peripherally restricted" if, upon administration to a subject, less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.1% of the compound crosses an intact blood brain barrier of the subject. In some embodiments, the term "peripherally restricted can mean that the concentration of a compound in the brain compared to the concentration in the circulating plasma (brain:plasma) ratio of about 1:5 or greater (e.g., about 1:10 or greater). In one exemplary embodiment the brain:plasma ratio is determined by measuring the ratio of a compound in mice or rats.

As used herein, the term "an effective amount" or "a therapeutically effective amount" refers to the amount of a compound that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "positive modulation" or "positive allosteric modulation" and all words stemming therefrom, refer to compounds that bind to an allosteric site on a receptor complex and affect it in a positive manner. Affecting a receptor in a positive manner typically means causing increased efficiency of the main receptor site. Increased receptor efficiency can mean potentially inducing a receptor to undergo a conformational change, or where the channel opens more frequently or for longer periods of time when an agonist binds to the receptor.

As used herein, "visceral pain" refers to pain that results from the activation of nociceptors of the thoracic, pelvic, or abdominal organs. Problems with organs, for example but not limited to, the stomach, kidney, gallbladder, urinary bladder, pancreas, and intestines, can lead to visceral pain. Such problems can include distension, perforation, inflammation, impaction, and constipation. The visceral pain can be diffuse, vague, dull, deep, squeezing, pressure-like, and difficult to localize. The visceral pain may be accompanied by symptoms such as nausea, vomiting, sweating, and changes in blood pressure, heart rate, and temperature. Visceral pain can often be experienced, or "referred" to different sites of the body. In some embodiments, visceral pain can be associated with functional dyspepsia, interstitial cystitis, chronic pancreatitis, or dysmenorrhea.

As used herein, "gut motility" refers to stretching and contractions of the muscles of the gastrointestinal tract. Peristaltic movement is the cyclical relaxation of circular smooth muscles, followed by their longitudinal contraction. Gut motility can be impaired, which can lead to abnormal contractions, including spasms and paralysis.

As used herein, "irritable bowel syndrome" or "IBS" generally refers to a syndrome in which subjects experience recurrent or chronic gastrointestinal symptoms. Symptoms of IBS can include, e.g., abdominal pain, abdominal discomfort, constipation, diarrhea, mucus in the stool, abdominal bloating, or a combination of any of the above. IBS may be diagnosed when a person has had abdominal pain or discomfort at least 3 times a month for the last 3 months without other disease or injury that could explain the pain. The pain or discomfort of IBS may occur with a change in stool frequency or consistency or be relieved by a bowel movement. IBS can be classified into four subtypes based on a subject's usual stool consistency. The four subtypes of IBS are: IBS with constipation (IBS-C), IBS with diarrhea (IBS-D), mixed IBS (IBS-M), and unsubtyped IBS (IBS-U). A subject with IBS-C may have hard or lumpy stools at least 25 percent of the time, may have loose or watery stools less than 25 percent of the time, or a combination of the two. A subject with IBS-D may have loose or watery stools at least 25 percent of the time, hard or lumpy stools less than 25 percent of the time, or a combination of the two. A subject with IBS-M may have hard or lumpy stools at least 25 percent of the time and loose or watery stools at least 25 percent of the time. A subject with IBS-U may have hard or lumpy stools less than 25 percent of the time, loose or watery stools less than 25 percent of the time, or a combination of the two. Constipation associated with IBS may be due to slow or delayed gastric motility. In some embodiments, the subject with IBS has experienced constipation. IBS can be diagnosed in a subject by any methods known in the art or otherwise described herein. For instance, IBS may be diagnosed by a health care provider. The health care provider may conduct a physical exam and may take a medical history of the subject. IBS may be diagnosed if a subject has exhibited one or more symptoms of IBS for at least 3, 4, 5, or 6 months, with one or more symptoms occurring at least three times a month for the previous 3 months. Additional tests that may be useful in the diagnosis of IBS include, but are not limited to: a stool test, lower GI series, flexible sigmoidoscopy, or colonoscopy.

The term "functional abdominal pain" or "functional abdominal pain syndrome" (FAPS) generally refers to a chronic and or frequently recurring pain not associated with changes in bowel movement patterns or with altered motility in the intestines. Normal abdominal activity may be experienced as being painful and contribute to functional abdominal pain. Functional abdominal pain may be related to central hypersensitivity, where the brain may fail to regulate pain signals from the gastrointestinal tract. While symptoms of FAPS can appear without apparent cause, they can also occur after infections or events that stimulate the bowel and also after traumatic life events like the death of a loved one, a divorce, or a history of sexual or physical abuse. During times of added stress, symptoms can worsen.

Repeated injury in the abdomen can cause nerve receptors to become overly sensitive. For instance, if someone has had multiple abdominal surgeries or an infection, a later painful occurrence may be experienced as more painful than previously. Even normal abdominal activity may be experienced as being painful. It is as if the volume has been turned up on a stereo receiver. This condition is called visceral hypersensitivity (i.e., increased sensitivity of the intestines). Furthermore although the brain has an ability to "turn down" the pain signals from the GI tract with FAPS, this ability is reduced, so even small amounts of intestinal disturbance can be amplified to produce severe pain (central hypersensitivity). So these individuals have an altered "braingut axis" where there is a failure of the brain to regulate even normal gut nerve activity leading to increased pain.

For purposes of this disclosure, the term "diarrhea," as used herein means frequent, poorly formed, loose, watery stools of a subject. A subject having diarrhea means the subject is passing loose stools at least three times a day. The term "acute diarrhea" is a common problem that usually lasts <7 days but can last in a protracted or prolonged form for <21 days. Diarrhea lasting more than 2 days is often a sign of an enteropathogenic infection. The term "chronic diarrhea" means diarrhea that lasts at least 4 weeks. Chronic diarrhea symptoms may be continual or intermittent. The term "traveler's diarrhea" means diarrheal symptoms associated with travel-related infection. It may be caused by many different organisms, including bacteria such as *E. coli, Salmonella, Shigella, Campylobacter, Aeromonas, Plesiomonas*, and vibrios; parasites such as *Giardia, Entamoeba histolytica, Cryptosporidium*, and *Cyclospora*; and viruses. In addition to diarrhea, symptoms may include nausea, vomiting, abdominal pain, fever, sweats, chills, headache, and malaise. Diarrhea may also be the result of food borne enteropathogens. Typical food borne pathogens are *E. coli, Salmonella, Shigella, Yersinia*, and *Campylobacter*.

Diarrhea of any duration may cause dehydration, which means the body lacks enough fluid and electrolytes-chemicals in salts, including sodium, potassium, and chloride—to function properly. Loose stools contain more water and electrolytes and often weigh more than solid stools.

The term "functional idiopathic diarrhea" generally refers to diarrhea occurring for unknown reasons. Idiopathic diarrhea generally lasts for less than 5 days and often resolves within 2 or 3 days. Diarrhea generally means an increased frequency or decreased consistency of bowl movements. Diarrhea can also mean an increase in stool weight.

The term "inflammatory bowel diseases" generally refers to chronic inflammation of all or part of the gastrointestinal tract. Symptoms of inflammatory bowel diseases can involve severe diarrhea, pain, abdominal pain and cramping, blood in the subject's stool, fatigue, reduced appetite and weight loss, or a combination of any of the above. Additional symptoms of inflammatory diseases also include bowel obstruction, ulcers, perforated colon, fistulas, anal fissure, malnutrition, severe dehydration, increased risk of colon cancer. Non limiting examples of inflammatory bowel diseases include Crohn's disease and ulcerative colitis, which itself may have several different subtypes, such as ulcerative proctitis, proctosigmoiditis, left-sided colitis, pancolitis, acute severe ulcerative colitis. Inflammatory bowel disease can be diagnosed in a subject by any methods known in the art or otherwise described herein. For instance, inflammatory bowel disease may be diagnosed by a health care provider. A physician or health care provider may perform or order a combination of tests to confirm the presence of inflammatory bowel disease, including, but not limited to, blood tests of anemia or infection, fecal occult blood test, colonoscopy, flexible sigmoidoscopy, upper endoscopy, capsule endoscopy, double-balloon endoscopy, x-ray, computerized tomography scan, magnetic resonance imaging, or small bowel imaging.

The term "drug induced pain" is the unintended effect of a drug, which results in symptoms sufficient to prompt a patient to seek medical attention and/or require hospitalization. Examples of medications that are known to induce pain include: chemotherapy drugs, which are known to cause nerve damage in the form of peripheral neuropathy. In fact, the onset of peripheral neuropathy can be the primary limiting factor for the amount and duration of the chemotherapy; cholesterol-lowering drugs that people take medications to lower cholesterol levels are known to cause muscle pain and weakness is well known to be a resulting side-effect from cholesterol-lowering drugs; and opioids (hydrocodone, hydromorphone, oxycodone, morphine) when used for years and the pain becomes worse, this vicious pain cycle can be a result of opioid-induced hyperalgesia.

Proteins, carbohydrates, fats, and most fluids are absorbed in the small intestine (small bowel). Malabsorption syndrome occurs when something prevents the bowel from absorbing important nutrients and fluids. The problem may be caused by inflammation, disease, or injury. Sometimes, the condition may be the result of the body's failure to produce enzymes needed to digest some foods. Factors that may cause malabsorption syndrome include: antibiotic use; conditions such as celiac disease, chronic pancreatitis, cystic fibrosis, and dairy protein allergies; congenital (birth) defects or diseases of the gall bladder, liver, or pancreas; damage to the intestine (from infection, inflammation, injury, or surgery); and radiation therapy (which may injure the mucosal lining of the bowel). Symptoms can include bloating, flatulence, or explosive diarrhea.

The term "bile salt malabsorption" generally refers increased bile salts in the gastrointestinal tract, which can cause fluid to be pumped into the colon, causing diarrhea. Other symptoms of bile salt malabsorption can also include cramping in the abdomen, smelly wind, weight loss, gall stones, and kidney stones. There are currently three recognized types of bile salt malabsorption: (1) bile salt malabsorption, secondary to ileal resection, or ileal inflammation, (2) idiopathic/primary bile salt malabsorption, and (3) secondary to various gastrointestinal diseases. Bile salt malabsorption can be diagnosed in a subject by any methods known in the art or otherwise described herein. For instance, bile salt malabsorption may be diagnosed by a health care provider. A physician or health care provider may perform or order a combination of tests to confirm the presence of bile salt malabsorption, including, but not limited to, a SeHCAT scan, measurement of 7 alpha-hydroxy-4-cholesten-3-one, and fasting blood FGF19 values.

The terms "treat" and "prevent" as well as words stemming therefrom, as used herein, refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. For prophylactic benefit, the compositions may be administered to a subject at risk of developing a particular disease, or to a subject reporting one or more of the physiological symptoms of a disease, even though a diagnosis of this disease may not have been made. Therefore, there are varying degrees of treatment or prevention of which one of ordinary skill in the art recognizes as having a potential benefit or therapeutic effect. In this respect, the inventive methods can provide any amount of any level of treatment or prevention of a GABA-A mediated disease in a mammal. Furthermore, the treatment or prevention provided by the inventive method can include treatment or prevention of one or more conditions or symptoms of a disease, e.g., IBS, being treated or prevented.

As used herein, the term "subject" refers to any mammal, including, but not limited to, mammals of the order Rodentia, such as mice and hamsters, and mammals of the order Logomorpha, such as rabbits. In some embodiments, the mammals are from the order Carnivora, including Felines (cats) and Canines (dogs). In some embodiments, the mammals are from the order Artiodactyla, including Bovines (cows) and Swines (pigs) or of the order Perssodactyla, including Equines (horses). In some embodiments, the mammals are of the order Primates, Ceboids, or Simoids (monkeys) or of the order Anthropoids (humans and apes). As a non-limiting example, the mammal can be a human. In some cases, the subject in not an adult. Accordingly, in some embodiments, the subject is a human.

The term "alkyl," as used herein, refers to a saturated hydrocarbon chain that is a straight chain or branched chain, containing the indicated number of carbon atoms. For example, $C_1$-$C_4$ alkyl group indicates that the group has from 1 to 4 (inclusive) carbon atoms in it. Similarly, $C_1$-$C_{10}$ alkyl group indicates that the group has from 1 to 10 (inclusive) carbon atoms in it. Unless stated otherwise specifically in the specification, an alkyl group is optionally substituted. The term "haloalkyl", as used herein, refers to an alkyl, in which one or more hydrogen atoms is/are replaced with an independently selected halo.

The term "alkylene" refers to a divalent alkyl (e.g., —$CH_2$—).

The term "alkenyl," as used herein, refers to a hydrocarbon chain that is a straight chain or branched chain, containing the indicated number of carbon atoms having one or more carbon-carbon double bonds. For example, $C_2$-$C_4$ alkenyl group indicates that the group has from 2 to 4 (inclusive) carbon atoms in it. Similarly, $C_2$-$C_{10}$ alkenyl group indicates that the group has from 2 to 10 (inclusive) carbon atoms in it. Unless stated otherwise specifically in the specification, an alkenyl group is optionally substituted.

The term "alkynyl," as used herein, refers to a hydrocarbon chain that is a straight chain or branched chain, containing the indicated number of carbon atoms having one or more carbon-carbon triple bonds. For example, $C_2$-$C_4$ alkynyl group indicates that the group has from 2 to 4 (inclusive) carbon atoms in it. Similarly, $C_2$-$C_{10}$ alkynyl group indicates that the group has from 2 to 10 (inclusive) carbon atoms in it. Unless stated otherwise specifically in the specification, an alkynyl group is optionally substituted.

The term "halo" or "halogen," as used herein, refers to fluoro, chloro, bromo, or iodo.

The term "cycloalkyl" or "carbocyclic ring", as used herein, refers to a stable non-aromatic monocyclic or polycyclic hydrocarbon radical consisting solely of carbon and hydrogen atoms, which may include fused or bridged ring systems, having from three to fifteen carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

The term "heterocyclyl", "heterocycloalkyl", or "heterocyclic ring" refers to a substituted or unsubstituted 3-, 4-, 5-, 6- or 7-membered saturated or partially unsaturated ring containing one, two, or three heteroatoms, independently selected from oxygen, nitrogen and sulfur (e.g., S, S(O), or S(O)$_2$); heterocyclyl may be unsubstituted or substituted with one or more substituents. The heterocyclyl may be optionally fused to another cycloalkyl, heterocyclyl, or an aryl. For example, to a benzo group.

The term "aryl", as used herein, refers to a hydrocarbon ring system radical comprising, e.g., 6 to 18 carbon atoms and at least one aromatic ring. The aryl radical can be a monocyclic, bicyclic, tricyclic, or tetracyclic ring system, which may include fused or bridged ring systems. Aryl radicals can include, but not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

The term "heteroaryl", as used herein, refers to a 5- to 14-membered ring system radical comprising one or more heteroatoms selected from the group consisting of nitrogen, oxygen, and sulfur (e.g., S, S(O), or S(O)$_2$). The heteroaryl radical may be a monocyclic, bicyclic, tricyclic, or tetracyclic ring system, which may include fused or bridged ring systems; the nitrogen, carbon or sulfur atoms in the heteroaryl radical may be optionally oxidized; and the nitrogen atom may be optionally quaternized. Exemplary heteroaryl groups may include, but not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

The term "alkoxy", as used herein, refers to an —O-alkyl radical (e.g., —OCH₃). The term "haloalkoxy", as used herein, refers to an —O-haloalkyl radical (e.g., —OCF₃).

The term "thioalkoxy", as used herein, refers to an —S-alkyl radical (e.g., —SCH₃). The term "halothioalkoxy", as used herein refers to an —S-haloalkyl radical (e.g., —SCF₃).

The term "C(O)glucuronic acid", as used herein, refers to a radical having formula:

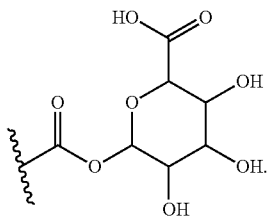 [SMILES: *C(=O)OC1OC(C(=O)O)C(O)C(O)C1O]

As a non-limiting example, the radical can be:

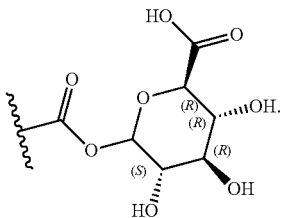

Atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Exemplary Pharmaceutical Compositions

Accordingly, included within the compounds of this disclosure are the tautomeric forms of the disclosed compounds, isomeric forms including enantiomers, stereoisomers, and diastereoisomers, and the pharmaceutically-acceptable salts thereof.

The salts of the compounds of Formula (I) used in the method of treatment described herein will be pharmaceutically acceptable salts. A person of ordinary skill in the art would recognize that non-pharmaceutically acceptable salts may be used as intermediaries in the preparation of the compounds of Formula (I) or its derivatives and their pharmaceutically acceptable salts. When the compound of this disclosure is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Non-limiting examples include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of this disclosure is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Non-limiting examples include citric, hydrobromic, hydrochloric, maleic, phosphoric, sulfuric and tartaric acids. In a further embodiment of this disclosure, a formulation comprising a compound of Formula (I), or a salt, solvate, or stereoisomer thereof, and a suitable pharmaceutically acceptable carrier is provided as understood by a person of ordinary skill in the art.

In yet a further aspect of this disclosure, a method for treating a patient with IBS is provided. The method comprises the steps of administering one or more compounds of Formula (I), or a salt, solvate, or stereoisomer thereof, or a derivative thereof to a subject. The compounds can be provided with a pharmaceutically acceptable carrier, when necessary.

Carriers and Excipients

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

In addition, in some embodiments, the compounds of this disclosure may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzalkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the compound in the composition comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.0001% of the pharmaceutical composition by w/w, w/v or v/v.

In some embodiments, the concentration of the compound is in the range of about 0.0001% to about 50%, about 0.001% to about 40%, about 0.01% to about 20%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% of the pharmaceutical composition by w/w, w/v or v/v.

In some embodiments, the concentration of the compound is in the range of about 0.0001% to about 5%, about 0.001% to about 4%, about 0.01% to about 2%, about 0.02% to about 1%, or about 0.05% to about 0.5% of the pharmaceutical composition by w/w, w/v or v/v.

In some embodiments, the amount of the compound in the pharmaceutical composition is about 0.00001 mg, 0.0001 mg, 0.001 mg, 0.005 mg, 0.01 mg, 0.05 mg, 0.1 mg, 0.25 mg, 0.5 mg, 1 mg, 2 mg, 4 mg, 8 mg, 10 mg, 12 mg, 14 mg, 16 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 1.1 g, 1.2 g, 1.3 g, 1.4 g, 1.5 g, 1.6 g, 1.7 g, 1.8 g, 1.9 g, 2 g, 2.5 g, 3 g, 3.5 g, 4 g, 4.5 g, 5 g, 6 g, 7 g, 8 g, 9 g, or 10 g.

Exemplary Modes of Administration

Administration of a pharmaceutical composition as described herein can be performed by any method that enables delivery of the compound to the site of action. The composition may be administered orally, parenterally, enterally, intraperitoneally, topically, transdermally, ophthalmically, intranasally, locally, non-orally, via spray, subcutaneously, intravenously, intratonsillary, intramuscularly, buccally, sublingually, rectally, intravaginally (e.g., via vaginal pessaries, e.g., using methods described in Capra et al. *Journal of Pharmaceutics* 2013, 386546, which is incorporated herein by reference in its entirety), intra-arterially, by infusion, or intrathecally. In some embodiments, the composition is administered orally. In some cases, the oral administration may comprise administration of any of the oral dosage forms as described herein. In some cases, a composition described herein is administered sublingually. In some cases, a composition described herein is administered transdermally, e.g., via transdermal patch. The effective amount of a compound administered will be dependent on the subject being treated, the severity of the disorder or condition, the rate of administration, the disposition of the compound and the discretion of the prescribing physician.

Pharmaceutical Compositions for Oral Administration

The pharmaceutical composition comprising an effective amount of a compound can be formulated for oral administration. In some embodiments, the pharmaceutical composition comprising an effective amount of a compound for oral administration is a solid pharmaceutical composition. In some embodiments, the solid pharmaceutical composition may be presented as discrete (e.g., unit) oral dosage forms. Non-limiting examples of discrete oral dosage forms include tablets, capsules, caplets, gelatin capsules, sustained release formulations, lozenges, thin films, lollipops, chewing gum. In some embodiments, the discrete oral dosage form is an orally disintegrating oral dosage form, such as, an orally disintegrating tablet.

In some embodiments, the pharmaceutical composition comprising an effective amount of a compound for oral administration is a liquid pharmaceutical composition. Non-limiting examples of liquid compositions for oral administration include hydrophilic suspensions, emulsions, liquids, gels, syrups, slurries, solutions, elixirs, softgels, tinctures, and hydrogels. In some embodiments, solid or liquid compositions comprising an effective amount of a compound for oral administration comprise various sweetening or flavoring agents, or coloring agents. Examples of coloring agents include dyes suitable for food such as those known as F.D. & C. dyes and natural coloring agents such as grape skin extract, beet red powder, beta carotene, annato, carmine, turmeric, paprika, and so forth. Derivatives, analogues, and isomers of any of the above colored compound also may be used.

The choice of carrier will be determined, in part, by the particular compound, as well as by the particular method used to administer the compound. Accordingly, there are a variety of suitable formulations of the pharmaceutical composition of this disclosure. The following formulations for parenteral, subcutaneous, intravenous, intramuscular, intraarterial, intrathecal and intraperitoneal administration are exemplary, and are in no way limiting. More than one route can be used to administer the compounds, and in certain instances, a particular route can provide a more immediate and more effective response than another route.
Pharmaceutical Compositions for Injection or Parenteral Administration Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. Non-limiting examples of liquid carriers (e.g., liquid carriers suitable for injectable solutions) include water, saline, aqueous dextrose and related sugar solutions, and glycols such as propylene glycols or polyethylene glycol. Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with this disclosure. The requirements for effective pharmaceutical carriers for injectable compositions are well-known to those of ordinary skill in the art (see, e.g., *Pharmaceutics and Pharmacy Practice*, J.B. Lippincott Company, Philadelphia, PA, Banker and Chalmers, eds., pages 238-250 (1982), and *ASHP Handbook on Injectable Drugs*, Trissel, 15th ed., pages 622-630 (2009)).
Other Pharmaceutical Compositions Alternatively, the compounds of this disclosure can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In some embodiments, the compounds of this disclosure provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially all of the compound is released immediately after administration.

In yet another embodiment, the compounds of this disclosure can be delivered in a controlled release system. For example, the agent may be administered using intravenous infusion, an implantable osmotic pump, a transdermal patch, or other modes of administration. In some embodiments, a pump may be used. In some embodiments, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

In some embodiments, the pharmaceutical compositions of this disclosure comprise the compounds of this disclosure, for example, the compounds disclosed herein, and/or their salts, solvates or stereoisomers thereof, and optionally, one or more additional therapeutic agents, such as, for example, 5-HT receptor inhibitors, antibiotics, anti-inflammatory, immunomodulators, together with a pharmaceutically acceptable carrier.

Examples of antibiotic agents suitable for use in pharmaceutical composition comprising the compounds heretofore described above and one or more antibiotic agents include, for example, quinolone antibiotics, such as levofloxacin, ciprofloxacin, ibafloxacin, pradofloxacin, rosoxacin, and sarafloxacin. Other suitable antibiotics are trimethoprim-sulfamethoxazole mixtures such as Bactrim®. Alternatives include rifaximin and azithromycin. Dosages vary with the weight and age of the subject to be treated. Typically, quinolone antibiotics and trimethoprim-sulfamethoxazole mixtures are given at dosages between 250 and 500 mg daily. For trimethoprim-sulfamethoxazole, the dosages are generally between about 5 mg/kg and 25 mg/kg. For rifaximin the dosage ranges from 100 mg to about 500 mg (e.g., 200 mg). Azithromycin is typically administered at 250-500 mg/day. The dosages required are well within the knowledge of those of ordinary skill in the art.

General Considerations

For purposes of this disclosure, the amount or dose of the compounds, salts, solvates, or stereoisomers of any one the compounds of Formula (I), as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds as set forth above, of this disclosure also will be determined by the existence, nature and extent of any adverse side effects that might accompany the administration of a particular compound.

Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit this disclosure, the dose of the compound can be about 0.001 to about 1000 mg/kg body weight of the subject being treated/day, from about 0.01 to about 100 mg/kg body weight/day, about 0.1 mg to about 10 mg/kg body weight/day. The several aspects of this disclosure, described above, are shown in the following examples.

EXAMPLES

Example 1: 8-chloro-6-(2-fluorophenyl)-4H-pyrazolo[1,5-a][1,4]benzodiazepine-2-carboxylic acid (Compound 101)

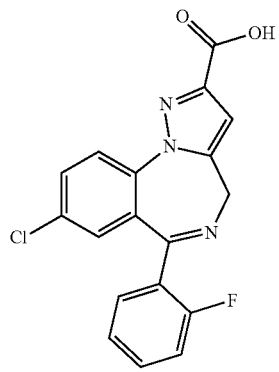

Method A

Step 1: ethyl 1-(4-chlorophenyl)-5-methyl-1H-pyrazole-3-carboxylate

A round bottom flask was charged with 4-chlorophenyl hydrazine HCl (31.47 g, 0.176 mol), MeOH (500 mL), ethyl 2,4-dioxopentanoate (24.69 mL, 1 eq.) and DIPEA (30.62 mL, 1 eq.). The mixture was heated to reflux for 1.5 hour. After completion, reaction mixture was cooled down to room temperature and silica gel (~70 g) was added. Solvent was evaporated and the silica deposit was subjected to flash chromatography on silica, eluting with 90% hexane:10% ethyl acetate. 26.4 g was obtained (56% yield). LC-MS ESI+: 265.10 (M+1).

Step 2: ethyl 1-(4-chloro-2-(2-fluorobenzoyl)phenyl)-5-methyl-1H-pyrazole-3-carboxylate Ethyl 1-(4-chlorophenyl)-5-methyl-1H-pyrazole-3-carboxylate (5.27 g, 0.02 mol) and 2-fluoro-benzaldehyde (4.19 mL, 2 eq.) were dissolved in 1,2-dichloroethane (73 mL) and placed in a screwed vial. To the resulting solution was added Pd(TFA)2 (662 mg, 0.1 eq.) and the mixture was stirred for 45 min at room temperature. TBHP (5.5 M in nonane, 9.05 mL, 2.5 eq.) was added in one portion. Reaction mixture was heated to 100° C. for 24 h. Then it was cooled down to room temperature and washed with 0.5 M NaOH (30 mL), dried over anhydrous MgSO4 and evaporated under reduced pressure. The product was purified using silica gel flash chromatography eluting with a gradient from 100% hexane to 80% hexane 20% ethyl acetate. 2.2 g was obtained (28%). LC-MS ESI+: 387.00 (M+1).

Step 3: ethyl 5-(bromomethyl)-1-(4-chloro-2-(2-fluorobenzoyl)phenyl)-1H-pyrazole-3-carboxylate Ethyl 1-(4-chloro-2-(2-fluorobenzoyl)phenyl)-5-methyl-1H-pyrazole-3-carboxylate (6.61 g, 0.017 mol) was dissolved in DCE (375 mL). Then NBS (3.65 g, 1.2 eq.) was added and the mixture was heated to 90° C. (oil bath temperature). After 5 minutes, Luperox A75 (0.55 g, 0.1 eq.) was added, and heating was continued. After 2 hours progress of the reaction was checked by LC-MS, approximately 40% of starting material was still present in the reaction mixture. An additional portion of NBS (1.82 g, 0.6 eq.) and benzoyl peroxide (0.27 g, 0.05 eq.) were added. Heating was continued for 1 hour. After that time TLC analysis showed almost full conversion of the starting material. The reaction mixture was cooled to room temperature and silica gel (~60 g) was added. Solvent was evaporated under reduced pressure. Product was purified using flash chromatography on silica, eluting with a gradient from 100% hexane to 80% hexane:20% ethyl acetate. 4.93 g was obtained (62% yield). LC-MS 464.95, 466.95 (M+1).

Step 4: ethyl 8-chloro-6-(2-fluorophenyl)-4H-benzo[f]pyrazolo[1,5-a][1,4]diazepine-2-carboxylate Ethyl 5-(bromomethyl)-1-(4-chloro-2-(2-fluorobenzoyl)phenyl)-1H-pyrazole-3-carboxylate (4.93 g, 0.106 mol) was dissolved in IPA (100 mL), together with ammonium acetate (3.59 g, 3 eq.) and urotropine (4.45 g, 3 eq.). RM was heated to reflux for 1.5 hours. Then RM was cooled to room temperature and silica gel (~50 g) was added. Solvent evaporated under reduced pressure. Product was purified using flash chromatography on silica, eluting with a gradient from 80%/hexane: 20% ethyl acetate to 50% hexane 50%/ ethyl acetate. 3.25 g was obtained (80%). LC-MS 384.05 (M+1).

Step 5: 8-chloro-6-(2-fluorophenyl)-4H-benzo[f] pyrazolo[1,5-a][1,4]diazepine-2-carboxylic Acid Ethyl 8-chloro-6-(2-fluorophenyl)-4H-benzo[f]pyrazolo [1,5-a][1,4]diazepine-2-carboxylate (3.25 g, 0.0085 mol) was dissolved in a THF:water mixture (v:v, 1:1, 84 mL), LiOH·H2O (1.93 g, 1.06 g, 3 eq.) was added in one portion and the reaction mixture was stirred at 60° C. temperature until completion, approximately 1 to 2 hours (indicated by TLC analysis, 100% ethyl acetate as eluent, SM Rf=0.6 and desired product DP Rf=0.0). After completion, THF was evaporated under reduced pressure. The water solution was acidified with formic acid to pH~5. The resulting precipitate was collected and washed with distilled water (100 mL). NOTE: if a very pure product is obtained in the previous step, no purification is required after saponification and acidification. Product was purified using $C_{18}$ reversed phase chromatography, eluting with a gradient from 90% water: 10% MeOH to 100% MeOH. 2.2 g was obtained (73%). LC-MS 355.90 (M+1). 1H NMR (400 MHz, DMSO-d6) δ 13.35-12.91 (s, 1H), 8.00 (d, J=8.8 Hz, 1H), 7.84 (dd, J=8.8, 2.4 Hz, 1H), 7.65-7.52 (m, 2H), 7.37-7.17 (m, 3H), 6.93 (s, 1H), 4.76 (s, 2H).

Examples 2-16 were Prepared According to Method A

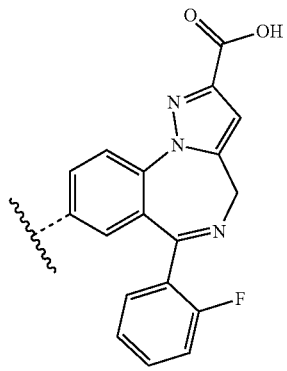

| Example | Name | R | Analytical data |
|---|---|---|---|
| 2 (Compound 102) | 8-ethynyl-6-(2-fluorophenyl)-4H-pyrazolo[1,5-a][1,4]benzodiazepine-2-carboxylic acid | ≡ | ESI(+): 346.25 (+H+). $^1$H NMR (400 MHz, DMSO-d6) δ 7.99 (d, J = 8.5 Hz, 1H), 7.84 (dd, J = 8.5, 1.9 Hz, 1H), 7.64-7.52 (m, 2H), 7.33 (ddd, J = 15.0, 7.5, 1.5 Hz, 2H), 7.26-7.19 (m, 1H), 6.89 (s, 1H), 4.75 (s, 2H), 4.36 (s, 1H). |
| 3 (Compound 103) | 8-cyclopropyl-6-(2-fluorophenyl)-4H-pyrazolo[1,5-a][1,4]benzodiazepine-2-carboxylic acid | ▷ | ESI(+): 362.07 (+H$^+$). $^1$H NMR (400 MHz, DMSO) δ 13.07 (s, 1H), 7.85 (d, J = 8.5 Hz, 1H), 7.55 (dddd, J = 17.0, 7.5, 6.4, 1.9 Hz, 2H), 7.40 (dd, J = 8.6, 2.1 Hz, 1H), 7.32 (td, J = 7.5, 1.1 Hz, 1H), 7.21 (ddd, J = 10.9, 8.2, 1.1 Hz, 1H), 6.98 (d, J = 2.0 Hz, 1H), 6.88 (s, 1H), 4.70 (s, 2H), 1.96 (tt, J = 8.3, 5.0 Hz, 1H), 1.01-0.92 (m, 2H), 0.63 (dt, J = 5.9, 3.3 Hz, 2H). |
| 4 (Compound 104) | 6-(2-fluorophenyl)-8-methyl-4H-pyrazolo[1,5-a][1,4]benzodiazepine-2-carboxylic acid | $H_3C$- | ESI(+): 335.95 (+H$^+$). $^1$H NMR (400 MHz, DMSO-d$_6$) δ 13.1 (s, 1H), 7.87 (d, J = 8.3 Hz, 1H), 7.65-7.46 (m, 3H), 7.32 (td, J = 7.5, 1.1 Hz, 1H), 7.20 (ddd, J = 10.8, 8.2, 1.1 Hz, 1H), 7.07 (d, J = 1.9 Hz, 1H), 6.87 (s, 1H), 4.73 (s, 2H), 2.32 (s, 3H). |

-continued

| | | | |
|---|---|---|---|
| 5 (Compound 105) | 6-(2-fluorophenyl)-4H-pyrazolo[1,5-a][1,4]benzodiazepine-2-carboxylic acid | H– | ESI(+): 321.7 (+H$^+$). $^1$H NMR (400 MHz, DMSO) δ 7.98 (dd, J = 8.3, 1.2 Hz, 1H), 7.76 (td, J = 8.4, 7.8, 1.5 Hz, 1H), 7.63-7.49 (m, 2H), 7.47 (td, J = 7.6, 1.2 Hz, 1H), 7.36-7.24 (m, 2H), 7.23-7.15 (m, 1H), 6.89 (s, 1H). |
| 6 (Compound 106) | 6-(2-fluorophenyl)-8-phenyl-4H-pyrazolo[1,5-a][1,4]benzodiazepine-2-carboxylic acid | Ph– | ESI(+): 398.06 (+H$^+$). $^1$H NMR (400 MHz, DMSO) δ 8.08 (d, J = 1.2 Hz, 2H), 7.65 (td, J = 7.7, 1.9 Hz, 1H), 7.62-7.57 (m, 2H), 7.57-7.43 (m, 5H), 7.42-7.36 (m, 1H), 7.33 (td, J = 7.5, 1.1 Hz, 1H), 7.24-7.12 (m, 1H), 6.94 (s, 1H). |
| 7 (Compound 107) | 8-bromo-6-(2-fluorophenyl)-4H-pyrazolo[1,5-a][1,4]benzodiazepine-2-carboxylic acid | Br– | ESI(+): 399.9, 402.9 $^1$H NMR (400 MHz, DMSO) δ 13.16 (s, 1H), 7.99-7.90 (m, 2H), 7.65-7.53 (m, 2H), 7.41 (d, J = 2.1 Hz, 1H), 7.34 (td, J = 7.5, 1.1 Hz, 1H), 7.23 (ddd, J = 10.9, 8.3, 1.1 Hz, 1H), 6.92 (s, 1H), 4.79 (s, 2H). |
| 8 (Compound 108) | 6-(2-fluorophenyl)-8-trimethylsilyl-4H-pyrazolo[1,5-a][1,4]benzodiazepine-2-carboxylic acid | (CH$_3$)$_3$Si– | ESI(+): 394.0 (+H$^+$). $^1$H NMR (400 MHz, DMSO) δ 7.99 (d, J = 8.1 Hz, 1H), 7.84 (dd, J = 8.1, 1.4 Hz, 1H), 7.62-7.48 (m, 2H), 7.36-7.27 (m, 2H), 7.19 (ddd, J = 10.8, 8.3, 1.1 Hz, 1H), 6.63 (s, 1H), 4.66 (s, 2H), 0.17 (s, 9H). |
| 9 (Compound 109) | 6-(2-fluorophenyl)-8-(trifluoromethylsulfanyl)-4H-pyrazolo[1,5-a][1,4]benzodiazepine-2-carboxylic acid | CF$_3$S– | ESI(+): found 421.95 (+H$^+$), calc. 421.05. $^1$H NMR (400 MHz, DMSO-d$_6$) δ 8.14 (d, J = 8.5 Hz, 1H), 8.09 (dd, J = 8.5, 2.1 Hz, 1H), 7.64 (td, J = 7.6, 1.8 Hz, 1H), 7.61-7.51 (m, 2H), 7.34 (td, J = 7.6, 1.1 Hz, 1H), 7.20 (ddd, J = 10.9, 8.3, 1.1 Hz, 1H), 6.96 (s, 1H), 4.80 (s, 2H). |
| 10 (Compound 110) | 6-(2-fluorophenyl)-8-(trifluoromethyl)-4H-pyrazolo[1,5-a][1,4]benzodiazepine-2-carboxylic acid | CF$_3$– | ESI(+): found 389.94 (+H$^+$), calc. 389.08 $^1$H NMR (400 MHz, DMSO-d$_6$) δ 8.21 (d, J = 8.6 Hz, 1H), 8.14 (dd, J = 8.7, 2.0 Hz, 1H), 7.66 (td, J = 7.7, 1.8 Hz, 1H), 7.61-7.52 (m, 2H), 7.35 (td, J = 7.5, 1.1 Hz, 1H), 7.22 (ddd, J = 10.9, 8.3, 1.1 Hz, 1H), 6.96 (s, 1H), 4.81 (s, 2H). |
| 11 (Compound 111) | 6-(2-fluorophenyl)-8-(trifluoromethoxy)-4H-pyrazolo[1,5-a][1,4]benzodiazepine-2-carboxylic acid | CF$_3$O– | ESI(+): found 405.97 (+H$^+$), calc. 405.07 $^1$H NMR (400 MHz, DMSO-d$_6$) δ 13.15 (s, 1H), 8.12 (d, J = 9.0 Hz, 1H), 7.85-7.76 (m, 1H), 7.64 (td, J = 7.6, 1.8 Hz, 1H), 7.57 (tdd, J = 7.5, 5.2, 1.8 Hz, 1H), 7.34 (td, J = 7.5, 1.1 Hz, 1H), 7.27-7.17 (m, 2H), 6.94 (s, 1H), 4.79 (s, 2H). |

-continued

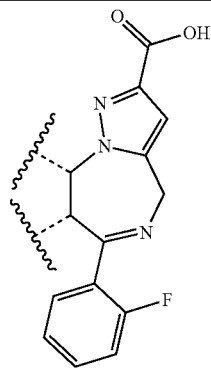

| Example | Name | R | Analytical Data |
|---|---|---|---|
| 12 (Compound 12) | 9-chloro-6-(2-fluorophenyl)-4H-pyrazolo[1,5-a][1]benzazepine-2-carboxylic acid | ![Cl-phenyl] | ESI(+): found 355.94 (+H+), calc. 355.05 $^1$H NMR (400 MHz, DMSO-d$_6$) δ 13.21 (s, 1H), 7.99 (d, J = 2.2 Hz, 1H), 7.64-7.50 (m, 3H), 7.37-7.29 (m, 2H), 7.21 (ddd, J = 10.9, 8.3, 1.1 Hz, 1H), 6.93 (s, 1H), 4.76 (s, 2H). |

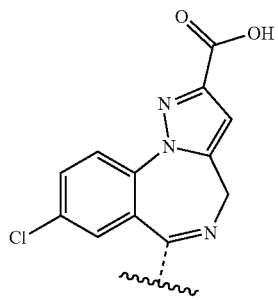

| Example | Name | R | Analytical Data |
|---|---|---|---|
| 13 (Compound 113) | 6-(2-bromophenyl)-8-chloro-4H-pyrazolo[1,5-a][1,4]benzodiazepine-2-carboxylic acid | 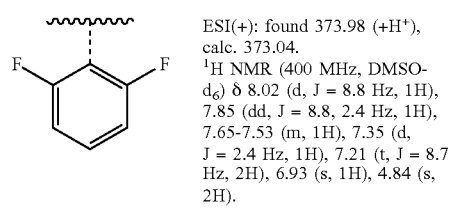 | ESI(+): found 415.9 (+H+), calc. 414.97. $^1$H NMR (400 MHz, DMSO-d$_6$) δ 8.00 (d, J = 8.8 Hz, 1H), 7.82 (dd, J = 8.8, 2.4 Hz, 1H), 7.62 (dt, J = 8.0, 1.5 Hz, 2H), 7.55 (d, J = 1.2 Hz, 1H), 7.42 (td, J = 7.7, 1.8 Hz, 1H), 7.06 (d, J = 2.3 Hz, 1H), 6.89 (s, 1H), 4.75 (s, 2H). |
| 14 (Compound 114) | 8-chloro-6-(2,6-difluorophenyl)-4H-pyrazolo[1,5-a][1,4]benzodiazepine-2-carboxylic acid | ![2,6-F2-phenyl] | ESI(+): found 373.98 (+H+), calc. 373.04. $^1$H NMR (400 MHz, DMSO-d$_6$) δ 8.02 (d, J = 8.8 Hz, 1H), 7.85 (dd, J = 8.8, 2.4 Hz, 1H), 7.65-7.53 (m, 1H), 7.35 (d, J = 2.4 Hz, 1H), 7.21 (t, J = 8.7 Hz, 2H), 6.93 (s, 1H), 4.84 (s, 2H). |
| 15 (Compound 115) | 8-chloro-6-(2-chlorophenyl)-4H-pyrazolo[1,5-a][1,4]benzodiazepine-2-carboxylic acid | 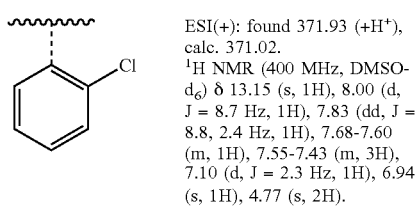 | ESI(+): found 371.93 (+H+), calc. 371.02. $^1$H NMR (400 MHz, DMSO-d$_6$) δ 13.15 (s, 1H), 8.00 (d, J = 8.7 Hz, 1H), 7.83 (dd, J = 8.8, 2.4 Hz, 1H), 7.68-7.60 (m, 1H), 7.55-7.43 (m, 3H), 7.10 (d, J = 2.3 Hz, 1H), 6.94 (s, 1H), 4.77 (s, 2H). |

| 16 (Compound 116) | 8-chloro-6-(2,3-difluorophenyl)-4H-pyrazolo[1,5-a][1]benzazepine-2-carboxylic acid | | ESI(+): found 373.95 (+H⁺), calc. 373.04<br>¹H NMR (400 MHz, DMSO-d₆) δ 8.01 (d, J = 8.8 Hz, 1H), 7.84 (dd, J = 8.8, 2.4 Hz, 1H), 7.66-7.51 (m, 1H), 7.43-7.26 (m, 3H), 6.81 (s, 1H), 4.75 (s, 2H). |
|---|---|---|---|
| 29 (Compound 129) | 8-chloro-6-phenyl-4H-benzo[f]pyrazolo[1,5-a][1,4]diazepine-2-carboxylic acid | | ESI(+): 338 (+H⁺),<br>¹H NMR (400 MHz, DMSO-d₆) δ 13.11 (s, 1H), 7.99 (d, J = 8.8 Hz, 1H), 7.87 (dd, J = 8.8, 2.4 Hz, 1H), 7.53-7.40 (m, 5H), 7.37 (d, J = 2.4 Hz, 1H), 6.90 (s, 1H), 5.20 (s, 1H), 4.21 (s, 1H). |

Example 17: 12-Chloro-9-(2-fluorophenyl)-2,3,8-triazatricyclo[8.4.0.0$^{2,6}$]tetradeca-1(10),3,5,8,11,13-hexaene-5-carboxylic Acid (Compound 117)

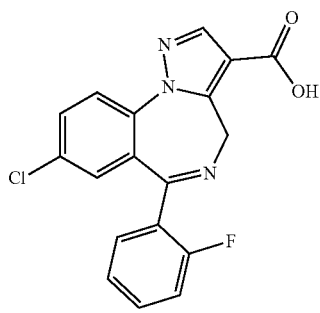 [SMILES: O=C(O)c1cnn2c1CN=C(c1ccccc1F)c1cc(Cl)ccc1-2]

Method B

Step 1: Ethyl 1-(4-chlorophenyl)-5-methyl-1H-pyrazole-4-carboxylate

Ethyl acetoacetate (8.06 mL, 1 eq.) was refluxed with N,N-dimethylformamide dimethyl acetal (10.19 mL, 1 eq.) for 1 hour. After cooling to room temperature the excess DMFDMA was distilled off under reduced pressure. The obtained residue was added to the solution of 4-chlorophenylhydrazine hydrochloride (8 g, 1 eq.) and DIPEA (8.56 mL, 1.1 eq.) in MeOH (100 mL). The resulting solution was refluxed for 3 hours. After cooling to room temperature the solvent was evaporated under reduced pressure. Obtained residue was dissolved in DCM (100 mL), washed with water (50 mL), dried over anhydrous magnesium sulfate and evaporated in vacuo. Product was purified using flash chromatography on silica, eluting with ethyl acetate. 7.38 g was obtained as a dark oil (62%). ESI(+): 265.05 (+H⁺).

Step 2: Ethyl 1-[4-chloro-2-(2-fluorobenzoyl)phenyl]-5-methyl-1H-pyrazole-4-carboxylate Ethyl 1-(4-chlorophenyl)-5-methyl-1H-pyrazole-4-carboxylate (4 g, 1 eq.) was dissolved in 1,2dichloroethane (20 mL). Palladium trifluoroacetate (0.5 g, 0.1 eq.) was added and the mixture was stirred for 40 minutes, until the solution became clear. Then, tert-butyl hydroperoxide solution (5-6 M in decane, 7.56 mL, 2.5 eq.) and 2-fluorobenzaldehyde (3.18 mL, 2 eq.) were added and the mixture was heated at 90° C. for 20 hours. After cooling to room temperature the reaction mixture was washed with water (20 mL), brine (2 mL), dried over anhydrous magnesium sulfate and evaporated in vacuo. The crude product was purified by silica gel chromatography, eluting with 80% hexane: 20% ethyl acetate. 3.4 g of a yellow solid was obtained (58%). ESI(+): 386.95 (+H⁺).

Step 3: Ethyl 5-(bromomethyl)-1-[4-chloro-2-(2-fluorobenzoyl)phenyl]-1H-pyrazole-4-carboxylate Ethyl 1-[4-chloro-2-(2-fluorobenzoyl)phenyl]-5-methyl-1H-pyrazole-4-carboxylate (1 g, 1 eq.) and N-bromosuccinimide (506 mg, 1.1 eq.) were dissolved in 1,2-dichloroethane (15 mL) and refluxed for 30 minutes. Then, dibenzoyl peroxide (125 mg, 0.15 eq.) was added in one portion and the reaction mixture was refluxed for 6 hours. After cooling to room temperature the solution was concentrated with silica gel (10 g), which was subjected to flash chromatography on silica, eluting with a gradient hexane:ethyl acetate 0%-20%. 483 mg of a white solid was obtained (40%). ESI(+): 464.85 (+H⁺).

Step 4: Ethyl 12-chloro-9-(2-fluorophenyl)-2,3,8-triazatricyclo[8.4.0.0$^{2,6}$]tetradeca-1(10),3,5,8,11,13-hexaene-5-carboxylate Ethyl 5-(bromomethyl)-1-[4-chloro-2-(2-fluorobenzoyl) phenyl]-1H-pyrazole-4-carboxylate (480 mg, 1 eq.), ammonium acetate (350 mg, 3 eq.) and urotropine (430 mg, 3 eq.) were dissolved in isopropanol (10 mL) and heated to reflux for 2 hours. After cooling to room temperature the solvent was evaporated and the residue was suspended in water (50 mL). The suspension was extracted with ethyl acetate (3×30 mL). Combined organic extracts were washed with brine (5 mL), dried over anhydrous MgSO₄ and evaporated to dryness under reduced pressure. The product was used in the next step without purification. 391 mg of a solid was obtained (98%). ESI(+): 383.95 (+H⁺).

Step 5: 12-Chloro-9-(2-fluorophenyl)-2,3,8-triazatricyclo[8.4.0.0$^{2,6}$]tetradeca-1(10),3,5,8,11,13-hexaene-5-carboxylic Acid Ethyl 12-chloro-9-(2-fluorophenyl)-2,3,8-triazatricyclo[8.4.0.0$^{2,6}$]tetradeca-1(10),3,5,8,11,13-hexaene-5-carboxylate (240 mg, 1 eq.) was dissolved in a mixture of THF and water 1:1 (6 mL). Lithium hydroxide monohydrate (77 mg, 3 eq.) was added in one portion and the mixture was stirred at 50° C. overnight. Then, THF was evaporated and the resulting solution was acidified with a dilute hydrochloric acid. Resulting precipitate was collected, washed with water (20 mL) and dried under reduced pressure. Solid was triturated with ethyl acetate. 130 mg of a white solid was obtained (59%). ESI(+): 356.00 (+H$^+$). $^1$H NMR (400 MHz, DMSO-d6) δ 12.94 (s, 1H), 8.20 (s, 1H), 8.00 (d, J=8.8 Hz, 1H), 7.85 (dd, J=8.8, 2.4 Hz, 1H), 7.67-7.50 (m, 2H), 7.39-7.27 (m, 2H), 7.27-7.17 (m, 1H), 5.01 (s, 2H).

Example 18 was Prepared According to Method B

| Example | Name | R | Analytical data |
|---|---|---|---|
| 18 (Compound 118) | 6-(2-fluorophenyl)-8-methyl-4H-pyrazolo[1,5-a][1,4]benzodiazepine-3-carboxylic acid | H$_3$C--- | ESI(+): 336.05 (+H$^+$). $^1$H NMR (400 MHz, DMSO) δ 8.15 (s, 1H), 7.87 (d, J = 8.3 Hz, 1H), 7.61-7.50 (m, 2H), 7.33 (dd, J = 7.5, 1.1 Hz, 1H), 7.20 (dd, J = 10.7, 8.2 Hz, 1H), 7.09 (d, J = 1.9 Hz, 1H), 2.32 (s, 3H), 2.08 (s, 1H). |

Example 19: 12-Chloro-9-(2-fluorophenyl)-5-methyl-2,3,8-triazatricyclo[8.4.0.0$^{2,6}$]tetradeca-1(10),3,5,8,11,13-hexaene-4-carboxylic Acid (Compound 119)

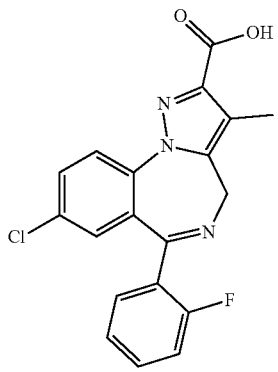 [SMILES: Cc1c(C(=O)O)nn2c1CN=C(c1ccccc1F)c1cc(Cl)ccc1-2]

Step 1: Ethyl 1-(4-chlorophenyl)-5-methyl-1H-pyrazole-3-carboxylate

Ethyl 2,4-dioxopentanoate (25 g, 1 eq.) and 4-chlorophenylhydrazine (22.54 g, 1 eq.) were dissolved in MeOH (600 mL). The resulting solution was refluxed for 1 hour. After cooling to room temperature the solvent was evaporated under reduced pressure. Product was purified using flash chromatography on silica, eluting with 90% hexane: 10% ethyl acetate. 19 g was obtained as a dark oil (45%). ESI(+): 265.05 (+H$^+$).

Step 2: Ethyl 1-[4-chloro-2-(2-fluorobenzoyl)phenyl]-5-methyl-1H-pyrazole-3-carboxylate Ethyl 1-(4-chlorophenyl)-5-methyl-1H-pyrazole-3-carboxylate (10.9 g, 1 eq.) was dissolved in 1,2dichloroethane (150 mL). Palladium trifluoroacetate (1.78 g, 0.1 eq.) was added and the mixture was stirred for 40 minutes, until the solution became clear. Then, tert-butyl hydroperoxide solution (5-6 M in decane, 18.72 mL, 2.5 eq.) and 2-fluorobenzaldehyde (8.67 mL, 2 eq.) were added and the mixture was heated at 90° C. for 20 hours. After cooling to room temperature the reaction mixture was washed with water (20 mL), brine (2 mL), dried over anhydrous magnesium sulfate and evaporated in vacuo. The crude product was purified by silica gel chromatography, eluting with 80% hexane: 20% ethyl acetate. 4.8 g of a yellow solid was obtained (30%). ESI(+): found 386.95 (+H$^+$).

Step 3: Ethyl 4-bromo-5-(bromomethyl)-1-[4-chloro-2-(2-fluorobenzoyl)phenyl]-1H-pyrazole-3-carboxylate Ethyl 1-[4-chloro-2-(2-fluorobenzoyl)phenyl]-5-methyl-1H-pyrazole-3-carboxylate (2.72 g, 1 eq.) and N-bromosuccinimide (2.75 mg, 2.2 eq.) were dissolved in 1,2-dichloroethane (150 mL) and refluxed for 30 minutes. Then, dibenzoyl peroxide (681 mg, 0.3 eq.) was added in one portion and the reaction mixture was refluxed for 6 hours. After cooling to room temperature the solution was concentrated with silica gel (50 g), which was subjected to flash chromatography on silica, eluting with a gradient hexane: ethyl acetate 0%-20%. 2.2 g of a light yellow solid was obtained (57%). ESI(+): 542.85 (+H$^+$).

Step 4: Ethyl 5-bromo-12-chloro-9-(2-fluorophenyl)-2,3,8-triazatricyclo[8.4.0.0$^{2,6}$]tetradeca-1(10),3,5,8,11,13-hexaene-4-carboxylate Ethyl 4-bromo-5-(bromomethyl)-1-[4-chloro-2-(2-fluorobenzoyl)phenyl]-1H-pyrazole-3-carboxylate (2.2 g, 1 eq.), ammonium acetate (1.37 g, 3 eq.) and urotropine (1.70 g, 3 eq.) were dissolved in isopropanol (40 mL) and heated to reflux for 2 hours. After cooling to room temperature the solvent was evaporated and the residue was suspended in water (50 mL). The suspension was extracted with ethyl acetate (3×30 mL). Combined organic extracts were washed with brine (5 mL), dried over anhydrous MgSO$_4$ and evaporated to dryness under reduced pressure. The crude product was purified by silica gel chromatography, eluting with 80% hexane: 20% ethyl acetate. 1.5 g of a solid was obtained (96%). ESI(+): 461.90 (+H$^+$).

Step 5: Ethyl 12-chloro-9-(2-fluorophenyl)-5-methyl-2,3,8-triazatricyclo[8.4.0.0$^{2,6}$]tetradeca-1(10),3,5,8,11,13-hexaene-4-carboxylate Ethyl 5-bromo-12-chloro-9-(2-fluorophenyl)-2,3,8-triazatricyclo[8.4.0.0$^{2,6}$]tetradeca-1(10),3,5,8,11,13-hexaene-4-carboxylate (1.14 g, 1 eq.), potassium methyltrifluoroborate (901 mg, 1.5 eq.), palladium chloride (70 mg, 0.16 eq.), triphenylphosphine (310 mg, 0.48 eq.) and cesium carbonate (2.41 g, 3 eq.) were placed in a screwed vial. THF (25 mL) and water (2.5 mL) were added, the reaction mixture was flushed with argon and heated to 120° C. for 4 days. After cooling to room temperature, the mixture was diluted with ethyl acetate (100 mL), washed with water (30 mL), brine (3 mL), dried over anhydrous magnesium sulfate and evaporated in vacuo. Product was purified by flash chromatography on silica eluting with a gradient hexane: ethyl acetate 0%-25%. 134 mg of a solid was obtained (13%). ESI(+): 397.90 (+H$^+$).

Step 6: 12-Chloro-9-(2-fluorophenyl)-5-methyl-2,3,8-triazatricyclo[8.4.0.0$^{2,6}$]tetradeca-1(10),3,5,8,11,13-hexaene-4-carboxylic Acid Ethyl 12-chloro-9-(2-fluorophenyl)-5-methyl-2,3,8-triazatricyclo[8.4.0.0$^{2,6}$]tetradeca-1(10),3,5,8,11,13-hexaene-4-carboxylate (180 mg, 1 eq.) was dissolved in a mixture of THF and water 1:1 (4 mL). Lithium hydroxide monohydrate (58 mg, 3 eq.) was added in one portion and the mixture was stirred at 50° C. overnight. Then, THF was evaporated and the resulting solution was acidified with a dilute hydrochloric acid. Resulting precipitate was collected, washed with water (20 mL) and dried under reduced pressure. Solid was triturated with ethyl acetate. 88 mg of a white solid was obtained (53%). ESI(+): 369.95 (+H$^+$). $^1$H NMR (400 MHz, DMSO-d6) δ 13.01 (s, 1H), 7.97 (d, J=8.8 Hz, 1H), 7.83 (dd, J=8.8, 2.4 Hz, 1H), 7.67-7.50 (m, 2H), 7.33 (td, J=7.5, 1.1 Hz, 1H), 7.28 (d, J=2.4 Hz, 1H), 7.22 (ddd, J=10.9, 8.3, 1.1 Hz, 1H), 4.70 (s, 2H), 2.30 (s, 3H).

Example 20: 12-Chloro-9-(2-fluorophenyl)-7-methyl-2,3,8-triazatricyclo[8.4.0.0$^{2,6}$]tetradeca-1(10),3,5,8,11,13-hexaene-4-carboxylic acid (Compound 120)

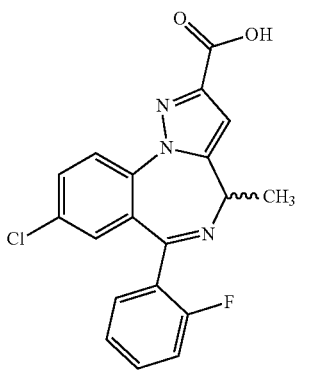 [SMILES: CC1N=C(c2ccccc2F)c2cc(Cl)ccc2-n2nc(C(=O)O)cc21]

Ethyl 12-chloro-9-(2-fluorophenyl)-2,3,8-triazatricyclo[8.4.0.0$^{2,6}$]tetradeca-1(10),3,5,8,11,13-hexaene-4-carboxylate (300 mg, 1 eq.) was placed in a heat gun dried three-necked round bottom flask and dissolved in anhydrous THF (8 mL). The atmosphere was evacuated and refilled with argon, thrice. The solution was cooled to −60° C. with a dry ice/acetone bath. KHMDS solution (1M in THF, 1 mL, 1.3 eq.) was added dropwise, after which the reaction mixture became deep red. After 20 minutes of stirring iodomethane (63 μL, 1.3 eq.) was added. The reaction was allowed to warm to room temperature and was stirred for 30 minutes. Next, solvent was evaporated under reduced pressure, the residue was dissolved in water (10 mL) and acidified with a dilute hydrochloric acid. The resulting precipitate was collected and washed with water (20 mL). Product was purified via preparative HPLC (C$_{18}$ column, mobile phase ACN+0.1% FA, H2O+0.1% FA). 60 mg of the product was obtained as a solid. (20% yield). ESI(+): 370.05 (+H$^+$). $^1$H NMR (400 MHz, DMSO-d6) δ 7.99 (d, J=8.8 Hz, 1H), 7.84 (dd, J=8.8, 2.4 Hz, 1H), 7.65-7.52 (m, 2H), 7.38-7.28 (m, 2H), 7.21 (ddd, J=10.9, 8.3, 1.1 Hz, 1H), 6.85 (s, 1H), 4.38 (q, J=6.9 Hz, 1H), 1.82 (d, J=6.7 Hz, 3H).

Example 21: 3-bromo-8-chloro-6-(2-fluorophenyl)-4H-pyrazolo[1,5-a][1,4]benzodiazepine-2-carboxylic Acid (Compound 121)

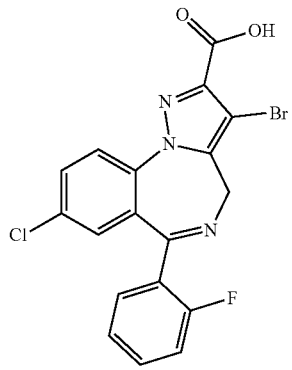 [SMILES: O=C(O)c1nn2c(c1Br)CN=C(c1ccccc1F)c1cc(Cl)ccc1-2]

Method C

Ethyl 4-bromo-5-(bromomethyl)-1-[4-chloro-2-(2-fluorobenzoyl)phenyl]-1H-pyrazole-3-carboxylate (500 mg, 1.1 mmol) was dissolved in a mixture of THF and water 1:1 (15 mL). Lithium hydroxide monohydrate (136 mg, 3 eq.) was added in one portion and the mixture was stirred at 50° C. overnight. Then, THF was evaporated and the resulting solution was acidified with a dilute hydrochloric acid. Resulting precipitate was collected, washed with water (35 mL) and dried under reduced pressure. Solid was triturated with ethyl acetate. 305 mg of a white solid was obtained (65%). ESI(+): 435.8, 437.9. $^1$H NMR (400 MHz, DMSO) δ 12.49 (s, 1H), 7.99 (d, J=8.8 Hz, 1H), 7.85 (dd, J=8.8, 2.4 Hz, 1H), 7.58 (dtd, J=21.0, 7.5, 1.7 Hz, 2H), 7.38-7.28 (m, 2H), 7.22 (dd, J=10.5, 8.4 Hz, 1H), 4.74 (s, 2H).

Example 22 was Prepared According to Method C

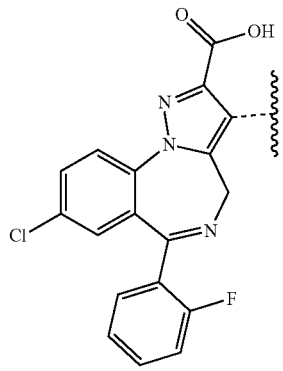

| Example | Name | R | Analytical data |
|---|---|---|---|
| 22 (Compound 122) | 3,8-dichloro-6-(2-fluorophenyl)-4H-pyrazolo[1,5-a][1,4]benzodiazepine-2-carboxylic acid | Cl—⋛ | ESI(+): 489.9, 391.9 ¹H NMR (400 MHz, DMSO) δ 13.54 (s, 1H), 8.01 (d, J = 8.7 Hz, 1H), 7.87 (dd, J = 8.8, 2.4 Hz, 1H), 7.66-7.52 (m, 2H), 7.39-7.30 (m, 2H), 7.23 (ddd, J = 10.9, 8.3, 1.1 Hz, 1H), 4.76 (s, 2H). |

Example 23: 8-chloro-6-(2-fluorophenyl)-5-oxido-4H-pyrazolo[1,5-a][1,4]benzodiazepin-5-ium-2-carboxylic Acid (Compound 123)

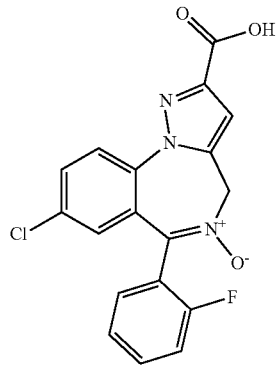 [SMILES: O=C(O)c1cc2n(n1)-c1ccc(Cl)cc1C(c1ccccc1F)=[N+]([O-])C2]

Step 1: 8-chloro-2-(ethoxycarbonyl)-6-(2-fluorophenyl)-4H-benzo[f]pyrazolo[1,5-a][1,4]diazepine 5-oxide To a stirring solution of ethyl 8-chloro-6-(2-fluorophenyl)-4H-benzo[f]pyrazolo[1,5-a][1,4]diazepine-2-carboxylate (250 mg, 0.54 mmol) in DCM (10 mL), m-CPBA (140 mg, 0.81 mmol) was added. The solution was stirred at room temperature overnight. Sodium sulfite solution (10%, 5 ml) was added. The solution was stirred at room temperature for 30 min. DCM (60 ml) was added. The solution was washed with sodium hydroxide solution (1 N, 2×30 ml), brine (30 ml), dried over sodium sulfate. The solution was filtered and concentrated. The residue was crystallized in methanol. The mother solution was purified by preparative HPLC to provide the desired product (171 mg, 73% yield) as white solid. ESI(+): 400 (+H⁺).

Step 2: 8-chloro-6-(2-fluorophenyl)-5-oxido-4H-pyrazolo[1,5-a][1,4]benzodiazepin-5-ium-2-carboxylic Acid To a screw-cap vial was added 8-chloro-2-(ethoxycarbonyl)-6-(2-fluorophenyl)-4H-benzo[f]pyrazolo[1,5-a][1,4]diazepine 5-oxide (100 mg, 0.25 mmol), followed by 6N hydrochloric acid (1 mL, 6 mmol). The resulting mixture was heated to 100° C. for 2 hours. After cooling to room temperature, the resulting precipitate was collected by filtration and sucked to dryness, affording the desired product as a colorless solid (12 mg, 13% yield). ESI(+): 369.69 (+H⁺). ¹H NMR (400 MHz, DMSO) δ 13.28 (s, 1H), 8.03 (d, J=8.8 Hz, 1H), 7.74 (dd, J=8.8, 2.4 Hz, 1H), 7.54 (dddd, J=8.5, 7.3, 5.4, 1.8 Hz, 1H), 7.48-7.24 (m, 3H), 7.12 (s, 1H), 7.03 (d, J=2.3 Hz, 1H), 5.41 (s, 2H).

Example 24: 8-chloro-6-(2-fluorophenyl)-4-hydroxy-4H-benzo[f]pyrazolo[1,5-a][1,4]diazepine-2-carboxylic Acid (Compound 124)

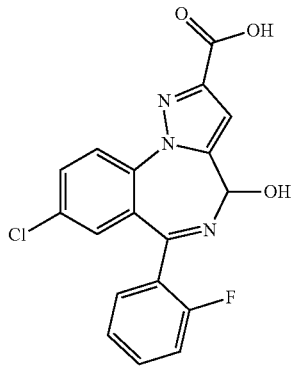 [SMILES: O=C(O)c1cc2n(n1)-c1ccc(Cl)cc1C(c1ccccc1F)=NC2O]

Step 1: ethyl 4-acetoxy-8-chloro-6-(2-fluorophenyl)-4H-benzo[f]pyrazolo[1,5-a][1,4]diazepine-2-carboxylate 8-chloro-2-(ethoxycarbonyl)-6-(2-fluorophenyl)-4H-benzo[f]pyrazolo[1,5-a][1,4]diazepine 5-oxide (70 mg, 0.18 mmol) was added to a screw-cap vial and dissolved in acetic anhydride (1.5 mL). The resulting mixture was heated to 70° C. for about 18 hours. Volatiles were evaporated under reduced pressure, and the resulting residue was triturated with about 5 mL of water. The resulting white precipitate was collected by filtration, rinsed with water and air dried to give the desired product (59 mg, 76% yield) as a solid. ESI(+): 442 (+H⁺).

Step 2: 8-chloro-6-(2-fluorophenyl)-4-hydroxy-4H-benzo[f]pyrazolo[1,5-a][1,4]diazepine-2-carboxylic Acid Ethyl 4-acetoxy-8-chloro-6-(2-fluorophenyl)-4H-benzo[f]pyrazolo[1,5-a][1,4]diazepine-2-carboxylate (59 mg, 0.13 mmol) was added to a screw-cap vial and dissolved in 6N HCl (1 mL, 6 mmol). The resulting mixture was heated to 100° C. for 3 hours. Volatiles were evaporated under reduced pressure, and the resulting residue was purified by preparative HPLC using a 5-95% gradient of water/acetonitrile, providing the desired product as a solid (32 mg, 64% yield). ESI(+): 371.92 (+H+). $^1$H NMR (400 MHz, DMSO) δ 9.65 (d, J=7.1 Hz, 1H), 7.89 (d, J=8.8 Hz, 1H), 7.72 (dd, J=8.7, 2.3 Hz, 1H), 7.29 (d, J=6.9 Hz, 1H), 7.18 (dd, J=11.2, 8.1 Hz, 1H), 7.07 (s, 1H), 6.99 (t, J=7.9 Hz, 1H), 6.79 (s, 1H), 5.98 (d, J=7.1 Hz, 1H).

Example 25: 8-chloro-6-(2-fluorophenyl)-N-(2-ureidoethyl)-4H-benzo[f]pyrazolo[1,5-a][1,4]diazepine-2-carboxamide (Compound 125)

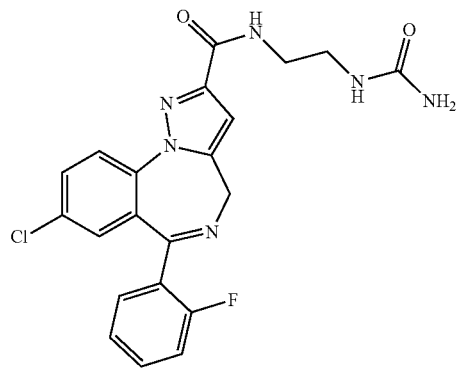 [SMILES: NC(=O)NCCNC(=O)c1cc2n(n1)-c1ccc(Cl)cc1C(c1ccccc1F)=NC2]

Method D

To a stirring solution of 8-chloro-6-(2-fluorophenyl)-4H-pyrazolo[1,5-a][1,4]benzodiazepine-2-carboxylic acid (150 mg, 0.4 mmol), 1-(2-Aminoethyl)urea hydrochloride (70.62 mg, 0.5 mmol), N,N-diisopropylethylamine (164 mg, 1.3 mmol) in DMF (2 mL), HBTU (192 mg, 0.5 mmol) was added. The solution was stirred at room temperature overnight. The solution was purified by preparative HPLC to give 8-chloro-6-(2-fluorophenyl)-N-(2-ureidoethyl)-4H-pyrazolo[1,5-a][1,4]benzodiazepine-2-carboxamide (140 mg, 75% yield) as white solid. ESI(+): 441. $^1$H NMR (400 MHz, DMSO-d6) δ ppm 3.00-3.36 (m, 4H) 6.13 (br. s., 1H) 6.86 (s, 1H) 7.09-7.39 (m, 3H) 7.47-7.67 (m, 2H) 7.76-7.93 (m, 1H) 8.06 (d, J=8.84 Hz, 1H) 8.44-8.59 (m, 1H).

Example 26: 8-chloro-6-(2-fluorophenyl)-N-(2-ureidoethyl)-4H-pyrazolo[1,5-a][1,4]benzodiazepine-3-carboxamide (Compound 126)

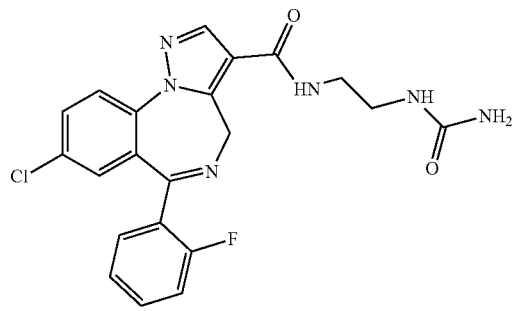 [SMILES: NC(=O)NCCNC(=O)c1cnn2c1CN=C(c1ccccc1F)c1cc(Cl)ccc1-2]

Method E

To a stirring solution of 8-chloro-6-(2-fluorophenyl)-4H-pyrazolo[1,5-a][1,4]benzodiazepine-3-carboxylic acid (150 mg, 0.4 mmol), 1-(2-Aminoethyl)urea hydrochloride (70.62 mg, 0.5100 mmol), N,N-diisopropylethylamine (163 mg, 1.3 mmol) in DMF (2 mL), HBTU (192 mg, 0.5 mmol) was added. The solution was stirred at room temperature overnight. The mixture was purified by preparative HPLC to give 8-chloro-6-(2-fluorophenyl)-N-(2-ureidoethyl)-4H-pyrazolo[1,5-a][1,4]benzodiazepine-3-carboxamide (81 mg, 0.2 mmol, 41% yield) as a white solid. ESI(+): 441. $^1$H NMR (400 MHz, DMSO-d6) δ ppm 3.15 (t, J=5.94 Hz, 2H) 3.21-3.33 (m, 2H) 7.15-7.26 (m, 1H) 7.26-7.38 (m, 2H) 7.50-7.67 (m, 2H) 7.79-7.91 (m, 1H) 7.93-8.03 (m, 1H) 8.32 (s, 1H) 8.37-8.50 (m, 1H)

Example 27: 8-chloro-6-(2-fluorophenyl)-N-[2-(sulfamoylamino)ethyl]-4H-pyrazolo[1,5-a][1,4]benzodiazepine-2-carboxamide (Compound 127)

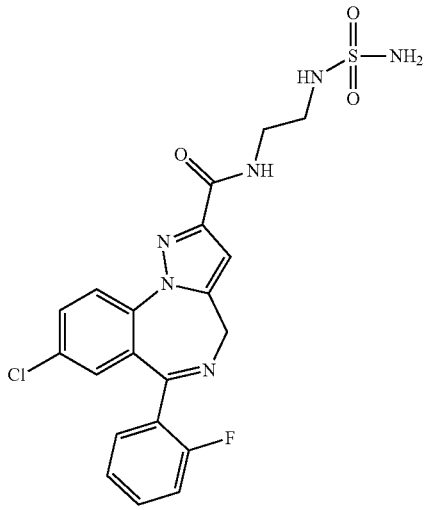 [SMILES: NS(=O)(=O)NCCNC(=O)c1cc2n(n1)-c1ccc(Cl)cc1C(c1ccccc1F)=NC2]

Step 1: tert-butyl N-[2-[[8-chloro-6-(2-fluorophenyl)-4H-pyrazolo[1,5-a][1,4]benzodiazepine-2-carbonyl]amino]ethyl]carbamate To a stirring solution of N-(2-aminoethyl)carbamic acid tert-butyl ester (0.6 g, 3.8 mmol), 8-chloro-6-(2-fluorophenyl)-4H-pyrazolo[1,5-a][1,4]benzodiazepine-2-carboxylic acid (1.1 g, 3.2 mmol), N,N-diisopropylethylamine (1.1 mL, 6.3 mmol) in DMF (20 mL), HBTU (1.4 g, 3.8 mmol) was added. The solution was stirred at room temperature overnight. Ethyl acetate (60 ml) was added. The solution was extracted with hydrochloric acid solution (1 N, 2×40 ml), water (40 ml), and brine (40 ml), dried over sodium sulfate. The solution was filtered and concentrated. The residue was purified by silica gel chromatography, eluting with methanol/dichloromethane (0-5%) to give tert-butyl N-[2-[[8-chloro-6-(2-fluorophenyl)-4H-pyrazolo[1,5-a][1,4]benzodiazepine-2-carbonyl]amino]ethyl]carbamate (1.5 g, 92% yield) as a colorless oil. ESI(+): 498. $^1$H NMR (400 MHz, DMSO-d6) δ ppm 1.30-1.40 (m, 9H) 2.69 (s, 1H) 2.85-2.93 (m, 1H) 3.11 (q, J=6.06 Hz, 2H) 3.30 (q, J=6.06 Hz, 2H) 5.77 (s, 2H) 6.86 (s, 1H) 6.94 (t, J=5.68 Hz, 1H) 7.18-7.26 (m, 1H) 7.29 (d, J=2.53 Hz, 1H) 7.32-7.38 (m, 1H) 7.52-7.66 (m, 2H) 7.87 (dd, J=8.72, 2.40 Hz, 1H) 8.04 (d, J=8.84 Hz, 1H) 8.45 (t, J=5.68 Hz, 1H).

Step 2: N-(2-aminoethyl)-8-chloro-6-(2-fluorophenyl)-4H-pyrazolo[1,5-a][1,4]benzodiazepine-2-carboxamide To a stirring solution of tert-butyl N-[2-[[8-chloro-6-(2-fluorophenyl)-4H-pyrazolo[1,5-a][1,4]benzodiazepine-2-carbonyl]amino]ethyl]carbamate (1.5 g, 2.9 mmol) in DCM (5 mL) at room temperature, TFA (5 mL, 2.9 mmol) was added. The solution was stirred at room temperature for three hours. The solution was concentrated. The residue was dissolved in dichloromethane (50 ml). The solution was extracted with sodium hydroxide solution (1 N, 2×20 ml), saturated sodium bicarbonate solution (20 ml), and brine (20 ml), dried over sodium sulfate. The solution was filtered and concentrated to give N-(2-aminoethyl)-8-chloro-6-(2-fluorophenyl)-4H-pyrazolo[1,5-a][1,4]benzodiazepine-2-carboxamide (1.3 g, 2.9 mmol, 99% yield) as a colorless oil. ESI(+): 398. $^1$H NMR (400 MHz, DMSO-d6) δ ppm 2.63-2.71 (m, 3H) 3.25 (q, J=6.32 Hz, 2H) 6.82-6.88 (m, 1H) 7.22 (ddd, J=10.86, 8.34, 0.76 Hz, 1H) 7.28 (d, J=2.27 Hz, 1H) 7.32-7.39 (m, 1H) 7.51-7.67 (m, 2H) 7.86 (dd, J=8.84, 2.27 Hz, 1H) 8.01-8.09 (m, 1H) 8.33 (s, 1H) 8.38 (t, J=5.81 Hz, 1H)

Step 3: 8-chloro-6-(2-fluorophenyl)-N-[2-(sulfamoylamino)ethyl]-4H-pyrazolo[1,5-a][1,4]benzodiazepine-2-carboxamide To a stirring solution of N-(2-aminoethyl)-8-chloro-6-(2-fluorophenyl)-4H-pyrazolo[1,5-a][1,4]benzodiazepine-2-carboxamide (170 mg, 0.4 mmol) in dioxane (2 mL), sulfamide (111 mg, 1.2 mmol) was added. The solution was heated at 100° C. overnight. After cooling down to room temperature, the solution was purified by preparative HPLC to give 8-chloro-6-(2-fluorophenyl)-N-[2-(sulfamoylamino)ethyl]-4H-pyrazolo[1,5-a][1,4]benzodiazepine-2-carboxamide (82 mg, 45% yield) as white solid. ESI(+): 477. $^1$H NMR (400 MHz, DMSO-d6) δ ppm 3.06 (t, J=6.57 Hz, 2H) 3.34-3.48 (m, 2H) 6.84-6.93 (m, 1H) 7.17-7.26 (m, 1H) 7.29 (d, J=2.27 Hz, 1H) 7.34 (td, J=7.52, 0.88 Hz, 1H) 7.51-7.68 (m, 2H) 7.82-7.92 (m, 1H) 8.01-8.10 (m, 1H) 8.50 (t, J=5.94 Hz, 1H)

Example 28: 8-chloro-6-(2-fluorophenyl)-N-[2-(sulfamoylamino)ethyl]-4H-pyrazolo[1,5-a][1,4]benzodiazepine-3-carboxamide (Compound 128)

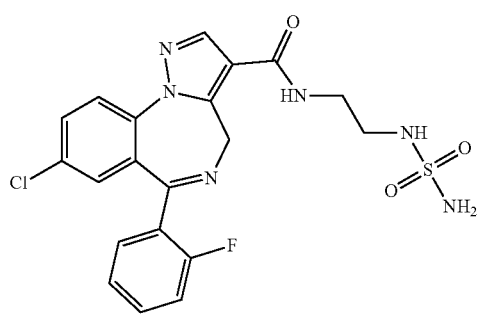 [SMILES: NS(=O)(=O)NCCNC(=O)c1cnn2c1CN=C(c1ccccc1F)c1cc(Cl)ccc1-2]

Step 1: tert-butyl N-[2-[[8-chloro-6-(2-fluorophenyl)-4H-pyrazolo[1,5-a][1,4]benzodiazepine-3-carbonyl]amino]ethyl]carbamate To a stirring solution of N-(2-aminoethyl)carbamic acid tert-butyl ester (0.8 g, 4.9 mmol), 8-chloro-6-(2-fluorophenyl)-4H-pyrazolo[1,5-a][1,4]benzodiazepine-3-carboxylic acid (1.5 g, 4.1 mmol), N,N-diisopropylethylamine (1.5 mL, 8.2 mmol) in DMF (20 mL), HBTU (1.9 g, 4.9 mmol) was added. The solution was stirred at room temperature overnight. Ethyl acetate (60 ml) was added. The solution was extracted with hydrochloric acid solution (1N, 2×40 ml), water (40 ml), and brine (40 ml), and dried over sodium sulfate. The solution was filtered and concentrated. The residue was purified by silica gel chromatography, eluting with methanol/dichloromethane (0-5%) to give tert-butyl N-[2-[[8-chloro-6-(2-fluorophenyl)-4H-pyrazolo[1,5-a][1,4]benzodiazepine-3-carbonyl]amino]ethyl]carbamate (2.3 g, 99% yield) as a colorless oil. ESI(+): 498. $^1$H NMR (400 MHz, DMSO-d6) δ ppm 1.26-1.42 (m, 9H) 2.99-3.14 (m, 2H) 3.26 (d, J=5.56 Hz, 2H) 3.36 (s, 2H) 5.72-5.81 (m, 1H) 7.22 (dd, J=10.86, 8.34 Hz, 1H) 7.27-7.38 (m, 2H) 7.51-7.67 (m, 2H) 7.83 (dd, J=8.84, 2.53 Hz, 1H) 7.90-8.03 (m, 2H) 8.23-8.41 (m, 2H).

Step 2: N-(2-aminoethyl)-8-chloro-6-(2-fluorophenyl)-4H-pyrazolo[1,5-a][1,4]benzodiazepine-3-carboxamide To a stirring solution of tert-butyl N-[2-[[8-chloro-6-(2-fluorophenyl)-4H-pyrazolo[1,5-a][1,4]benzodiazepine-3-carbonyl]amino]ethyl]carbamate (2.3 g, 4.1 mmol) in DCM (25 mL) at room temperature, TFA (25 mL, 4.1 mmol) was added. The solution was stirred at room temperature overnight. The solution was concentrated. The residue was dissolved in DCM (200 ml). The solution was extracted with sodium hydroxide solution (1.0 N, 2×50 ml), water (2×50 ml), and brine (50 ml), dried over sodium sulfate. The solution was filtered and concentrated to give N-(2-aminoethyl)-8-chloro-6-(2-fluorophenyl)-4H-pyrazolo[1,5-a][1,4]benzodiazepine-3-carboxamide (1.4 g, 87% yield) as a colorless oil which was used to the next step without purification. ESI(+): 398. $^1$H NMR (400 MHz, DMSO-d6) δ ppm 2.67 (br. s., 2H) 3.24 (q, J=6.23 Hz, 2H) 7.16-7.26 (m, 1H) 7.29 (d, J=2.27 Hz, 1H) 7.34 (td, J=7.58, 1.01 Hz, 1H) 7.52-7.66 (m, 2H) 7.78-7.86 (m, 1H) 7.92-8.01 (m, 1H) 8.29 (t, J=5.56 Hz, 1H) 8.33 (s, 1H) 8.36 (s, 1H)

Step 3: 8-chloro-6-(2-fluorophenyl)-N-[2-(sulfamoylamino)ethyl]-4H-pyrazolo[1,5-a][1,4]benzodiazepine-3-carboxamide To a stirring solution of N-(2-aminoethyl)-8-chloro-6-(2-fluorophenyl)-4H-pyrazolo[1,5-a][1,4]benzodiazepine-3-carboxamide (150 mg, 0.4 mmol) in dioxane (2 mL), sulfamide (109 mg, 1.1 mmol) was added. The solution was heated at 110° C. for 24 hours. After cooling down to room temperature, the solution was purified by preparative HPLC to give 8-chloro-6-(2-fluorophenyl)-N-[2-(sulfamoylamino)ethyl]-4H-pyrazolo[1,5-a][1,4]benzodiazepine-3-carboxamide (83 mg, 44% yield) as a lightly colored solid. ESI(+): 477. $^1$H NMR (400 MHz, DMSO-d6) δ ppm 3.05 (t, J=6.69 Hz, 2H) 3.32-3.47 (m, 2H) 7.14-7.25 (m, 1H) 7.26-7.38 (m, 2H) 7.49-7.66 (m, 2H) 7.78-7.90 (m, 1H) 7.91-8.03 (m, 1H) 8.26-8.35 (m, 1H) 8.35-8.48 (m, 1H)

Example B1

Modulatory effects of the compounds of this disclosure were investigated using cells stably transfected with GABA-activated channels of the GABA$_A$ ($\alpha_3\beta_2\gamma_2$) subtype together with submaximal GABA concentrations. Expression of GABA receptor were induced by adding Dexamethasone to the cells for 24 to 48 h before experimentation. In general, cells were passaged at a confluence of about 80 to 90%. For electrophysiological measurements cells were harvested at a confluence of about 80 to 90% from sterile culture flasks containing culture complete medium. Cells were transferred as suspension in PBS to the QPatch 16X or QPatch HTX system to the centrifuge/washer directly. Cells were incubated at 37° C. in a humidified atmosphere with 5% $CO_2$ (rel. humidity about 95%). The cells were continuously maintained in and passaged in sterile culture flasks containing a 1:1 mixture of Dulbecco's modified eagle medium and nutrient mixture D-MEM/F-12 (1×, liquid, with L-Glutamine), supplemented with 10% foetal bovine serum and 1.0% Penicillin/Streptomycin solution and neomycin. The 1× bath solution was made at least every 5 days out of a sterile lox bath solution, which had been prepared prior to the experimental start of the present study and stored at 1° C. to 9° C. The final bath solution included Sodium Chloride 137 mM, Potassium Chloride 4 mM, Calcium Chloride 1.8 mM, Magnesium Chloride 1 mM, HEPES 10 mM, D-Glucose 10 mM, pH (NaOH) 7.4. The 1× intracellular solution was thawed every day and includes Potassium Chloride 130 mM, Magnesium Chloride 1 mM, Mg-ATP 5 mM, HEPES 10 mM, EGTA 5 Mm, pH (KOH) 7.2. Automated patch-clamping: Cells were transferred as suspension in serum-free medium to the QPatch HTX system and kept in the cell storage tank during experiments. All solutions applied to cells including the intracellular solution were maintained at room temperature (19° C. to 30° C.). After formation of a Gigaohm seal between the patch electrodes and transfected individual Ltk cells were ruptured to assure electrical access to the cell interior (whole-cell patch-configuration). Inward currents were measured upon application of 2.0 μM GABA to patch-clamped cells for 4 s. During the entire experiment the cells were voltage-clamped at a holding potential of −80 mV. For the analysis of test items, $GABA_A$ receptors were stimulated by 2.0 μM GABA and test item combinations described below. Thirty-second prewash steps with test items was performed in between two agonist applications. The dose-response curve was fit with a sigmoidal three parameter equation current=Emax/1+10^((Log EC50−X)*H) where X is the compound concentration, $E_{max}$ the upper asymptote, $EC_{50}$ the concentration of test item at half maximal effect, and H is the Hill coefficient. SigmaPlot 11.0 was used for construction of curve. Data for exemplary compounds are provided below, in Table B1.

TABLE B1

| Example No. | Compound # | GABA $\alpha_3\beta_2\gamma_2$ $E_{max}$ |
|---|---|---|
| 1 | 101 | +++ |
| 2 | 102 | +++ |
| 3 | 103 | +++ |
| 4 | 104 | +++ |
| 5 | 105 | + |
| 6 | 106 | + |
| 7 | 107 | +++ |
| 8 | 108 | + |
| 9 | 109 | +++ |
| 10 | 110 | +++ |
| 11 | 111 | +++ |
| 12 | 112 | + |
| 13 | 113 | +++ |
| 14 | 114 | ++ |
| 15 | 115 | +++ |
| 16 | 116 | +++ |
| 17 | 117 | +++ |
| 18 | 118 | +++ |
| 19 | 119 | +++ |

TABLE B1-continued

| Example No. | Compound # | GABA $\alpha_3\beta_2\gamma_2$ $E_{max}$ |
|---|---|---|
| 20 | 120 | +++ |
| 21 | 121 | +++ |
| 22 | 122 | ++ |
| 23 | 123 | +++ |
| 24 | 124 | + |
| 25 | 125 | ++ |
| 26 | 126 | +++ |
| 27 | 127 | ++ |
| 28 | 128 | +++ |
| 29 | 129 | +++ |

Key:
+ $E_{max}$ <50%;
++ $E_{max}$ 51-100%;
+++ $E_{max}$ >100%

Example B2: Effects of the Compounds and Methods of this Disclosure on Whole Gut Transit Time Dose responses of the effect of Formula (I) compounds on the whole gut transit time (WGTT) are examined. A compound of Formula (I) (0, 1, 3 and 10 mg/kg) in 50%/propylene glycol is administrated by gavage (5 ml/kg), followed by gavage of 0.2 ml carmine red solution (6% carmine red in 0.5% methylcellulose) into C57B/6 mice. Mice are then placed in a white cardboard box and the time is recorded as time 0. The color of stool is observed every 10 min until the red dye appears in stool. The time that first red stool appears is recorded as the ending time. The difference between the ending time and time 0 is used to present WGTT (min).

Example B3: Effects on Distal Colon Transit Time

The time course of a compound of Formula (I) on distal colon transit time (DCTT) in C57B/6 mice is examined to assess the colon motility. DCTT is performed by gently pushing a 2 mm glass bead into rectal 2 cm and then placing the mouse into a white box (time 0). The time that the glass bead is released from rectal is presented as DCTT (min). Mice are gavaged with 0 or 3 mg/kg of a compound of Formula (I) and DCTT is conducted at 30, 60, 90 and 120 min after the administration of a compound of Formula (I).

Example B4. Effects on Stool Composition

After gavage of a compound of Formula (I) (3 and 10 mg/kg), stools are collected immediately after expulsion for 3 hours. The wet stools are weighted as total stool weight followed by dry at 65° C. for 24 hours and weight as dry stool weight. The percent of water content in the stool is calculated by (total stool weight−dry stool weighty total stool weight×100.

Example B5: Pain Sensitivity in IBS Mouse Model

IBS visceral pain model, induced by neonatal rectal irritation, is used. Colonic pain sensitivity to graded colorectal balloon distension (CRD, 15, 30, 50 and 70 mmHg) is determined by visceromotor response (VMR) measured by electromyography of external oblique muscle. IBS mice show a significant increase in pain sensitivity relative to control mice. IBS mice are treated with a compound of Formula (I) (10 mg/kg). Hyperalgesia in IBS mice is then examined.

Example B6: Measurement of Brain and Plasma Levels

A compound of Formula (I) is administered to 5 mice at a dose of 10 mg/kg as a solution in 50% propylene glycol by oral gavage (5 ml/kg). After 30 minutes, mice are sacrificed and plasma and brain are harvested. The concentration of the Formula (I) compound in plasma and brain are measured by LC/MS. Average plasma concentrations and brain concentration are examined.

Example B7: Measurement of GABA-A Binding

Potency at the GABA-A receptor is measured by [$^3$H] flunitrazepam binding to rat cerebral cortex tissue homogenate as described in Speth, R. C, Wastek, G. J., Johnson, P. C., Yamamura, H. I. "Benzodiazepine binding in human brain: Characterization using [$^3$H]flunitrazepam" *Life Sciences* 1978, 22, 859-866 (incorporated herein by reference in its entirety) and performed at CEREP (catalog number 0028).

The following references cited above are incorporate herein by reference in their entirety:
1. Everhart J E. The burden of digestive diseases in the United States. US Government Printing Office (NIH Publication No. 09-6443), 2008.
2. Sullivan M A, Cohen S, Snape W J, Jr. Colonic myoelectrical activity in irritable-bowel syndrome. Effect of eating and anticholinergics. N Engl J Med 1978; 298:878-83.
3. Gershon M D. Serotonin and its implication for the management of irritable bowel syndrome. Rev Gastroenterol Disord 2003; 3 Suppl 2:S25-34.
4. Pasricha P J. Desperately seeking serotonin. A commentary on the withdrawal of tegaserod and the state of drug development for functional and motility disorders. Gastroenterology 2007; 132:2287-90.
5. Fargeas M J, Fioramonti J, Bueno L. Central and peripheral action of GABAA and GABAB agonists on small intestine motility in rats. European Journal of Pharmacology 1988; 150:163-169.
6. Grider J R. Interplay of somatostatin, opioid, and GABA neurons in the regulation of the peristaltic reflex. American Journal of Physiology—Gastrointestinal and Liver Physiology 1994; 267:G696-G701.
7. Kerr D I B, Ong J. GABA and GABA-receptors in the enteric nervous system. Neuropharmacology 1984; 23:835-836.
8. Krantis A. GABA in the mammalian enteric nervous system. News in Physiological Sciences 2000; 15:284-290.
9. Krantis A, Costa M, Furness J B, Orbach J. γ-Aminobutyric acid stimulates intrinsic inhibitory and excitatory nerves in the guinea-pig intestine. European Journal of Pharmacology 1980; 67:461-466.
10. Ong J, Kerr D I B. Evidence for a physiological role of GABA in the control of guinea-pig intestinal motility. Neuroscience Letters 1984; 50:339-343.
11. Reis H J, Berghe P V, Romano-Silva M A, Smith T K. GABA-induced calcium signaling in cultured enteric neurons is reinforced by activation of cholinergic pathways. Neuroscience 2006; 139:485-494.
12. Williamson S, Faulkner-Jones B E, Cram D S, Furness J B, Harrison L C. Transcription and translation of two glutamate decarboxylase genes in the ileum of rat, mouse and guinea pig. Journal of the Autonomic Nervous System 1995; 55:18-28.
13. Williamson S, Pompolo S, Furness J B. GABA and nitric oxide synthase immunoreactivities are colocalized in a subset of inhibitory motor neurons of the guinea-pig small intestine. Cell and Tissue Research 1996; 284:29-37.
14. Salari P, Abdollahi M. Systematic review of modulators of benzodiazepine receptors in irritable bowel syndrome: is there hope? World J Gastroenterol 2011; 17:4251-7.
15. Ritchie J A, Truelove S C. Treatment of irritable bowel syndrome with lorazepam, hyoscine butylbromide, and ispaghula husk. Br Med J 1979; 1:376-8.
16. Pace F, Maurano A, Ciacci C, Savarino V, Attili A, Iaquinto G, Magni E, Porro G B. Octatropine methyl bromide and diazepam combination (Valpinax) in patients with irritable bowel syndrome: a multicentre, randomized, placebo-controlled trial. Eur Rev Med Pharmacol Sci 2010; 14:155-62.
17. Talley N J. Evaluation of drug treatment in irritable bowel syndrome. British Journal of Clinical Pharmacology 2003; 56:362-369.
18. Horvath K, Andrasi F, Berzsenyi P, Patfalusi M, Patthy M, Szabo G, Sebestyen L, Bagdy E, Korosi J, Botka P, Hamori T, Lang T. A New Psychoactive 5h-2,3-Benzodiazepine with a Unique Spectrum of Activity. Arzneimittel-Forschung/Drug Research 1989; 39-2:894-899.
19. Mennini T, Abbiati A, Caccia S, Cotecchia S, Gomez A, Garattini S. Brain Levels of Tofizopam in the Rat and Relationship with Benzodiazepine Receptors. Naunyn-Schmiedebergs Archives of Pharmacology 1982; 321: 112-115.
20. Bagal S K, Bungay P J. Minimizing Drug Exposure in the CNS while Maintaining Good Oral Absorption. Acs Medicinal Chemistry Letters 2012; 3:948-950.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing this disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate this disclosure and does not pose a limitation on the scope of this disclosure unless otherwise claimed. No language in the specification should be construed as indicating any non-claimed element as essential to the practice of this disclosure.

Preferred embodiments of this disclosure are described herein, including the best mode known to the inventors for carrying out this disclosure. Variations of those preferred embodiments may become apparent to those of ordinary skill in the art upon reading the foregoing description. The inventors expect skilled artisans to employ such variations as appropriate, and the inventors intend for this disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by this disclosure unless otherwise indicated herein or otherwise clearly contradicted by context.

What is claimed is:

1. A compound of Formula (I):

Formula (I)

or a pharmaceutically acceptable salt thereof, wherein:

- $R^{1a}$ is H, halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl;
- $R^{1b}$ is H, halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl;
- $R^{1c}$ is H, halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl;
- $R^{1d}$ is H, halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl;
- each $R^2$ is independently halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $OC_{1-6}$ alkyl, $OC_{1-6}$ haloalkyl, $S(NH)(O)C_{1-6}$ alkyl, $S(O)_2C_{1-6}$ alkyl, or $C_{3-6}$ cycloalkyl;
- m is 1, 2, 3, 4, or 5;
- (i) $R^{3a}$ is X; and
  $R^{3b}$ is $R^3$; or
- (ii) $R^{3a}$ is $R^3$; and
  $R^{3b}$ is X;
- $R^3$ is H, halo, CN, $C_{1-6}$ alkyl, $CH_2NR^6R^7$, $C_{1-6}$ haloalkyl, $C_{2-6}$ alkenyl, $C_{2-6}$ alkynyl, $C(O)NR^6R^7$, $NR^6R^7$, $OC_{1-6}$ alkyl, $OC_{1-6}$ haloalkyl, $C_{3-6}$ cycloalkyl, $C_{6-10}$ aryl, or 5- or 6-membered heteroaryl, wherein the 5- or 6-membered heteroaryl contains 1, 2, 3, or 4 ring heteroatoms or heteroatomic groups independently selected from the group consisting of N, $NR^8$, O, and S;
- (iii) X is $C_{1-3}$ alkylene-$N^+(C_{1-3}$ alkyl$)_3$, $CH(R^X)C(O)Y$, $CH(R^X)C(O)OH$, $CH(R^X)S(O)_2Y$, $C(O)Y$, $C(O)OH$, $C(O)$glucuronic acid, $P(O)(OH)_2$, $S(O)_2Y$, or $S(O)_2OH$; or
- (iv) X is:

- $R^X$ is H, $C_{1-6}$ alkyl, $NR^6R^7$, or OH;
- $X^A$ is —NH—, —N($C_{1-3}$ alkyl)-, —O—, or —S—;
- $X^B$ is —NH—, —N($C_{1-3}$ alkyl)-, —O—, or —S—;
- Y is $NR^6R^7$, $NR^8CH_2CH_2O(CH_2CH_2O)_nY^4$, or $NR^8Y^2Y^3$;
- $Y^2$ is $C_{2-6}$ alkylene;
- $Y^3$ is $NR^6R^7$, $NR^9S(O)_2NR^9R^{10}$, $P(O)(C_{1-3}$ alkyl$)_2$, $S(NR^8)(O)R^6$, or $S(O)_2R^6$;
- $Y^4$ is H or $C_{1-6}$ alkyl;
- n is 0, 1, 2, 3, 4, 5, 6, 7, 8, 9, 10, 11, 12, 13, 14, 15, 16, 17, 18, 19, or 20;
- $R^4$ is H, $C_{1-6}$ alkyl, $NR^6R^7$, or OH;
- $R^5$ is H, $C_{1-6}$ alkyl, $NR^6R^7$, or OH;
- each $R^6$ is independently H, $C_{1-6}$ alkyl, $C_{1-6}$ haloalkyl, $C_{1-4}$ alkylene-phenyl, $C(O)R^9$, $C(O)NR^9R^{10}$, $C(O)OR^9$, $C_{3-6}$ cycloalkyl, or phenyl;
- each $R^7$ is independently H, $C_{1-6}$ alkyl, $C_{1-6}$ haloalkyl, $C_{1-4}$ alkylene-phenyl, $C(O)R^9$, $C(O)NR^9R^{10}$, $C(O)OR^9$, $C_{3-6}$ cycloalkyl, or phenyl; or
- any $R^6$ and $R^7$, taken together with the nitrogen atom to which they are attached, independently forms a saturated, partially unsaturated, or aromatic 4- to 8-membered ring, wherein the 4- to 8-membered ring contains 0, 1, or 2 additional ring heteroatoms or heteroatomic groups independently selected from the group consisting of N, $NR^8$, O, and S;

each $R^8$ is independently H, $C_{1-6}$ alkyl, $C(O)R^9$, $C(O)NR^9R^{10}$, or $C(O)OR^9$;

each $R^9$ is independently H or $C_{1-6}$ alkyl;

each $R^{10}$ is independently H or $C_{1-6}$ alkyl; and

Z is N.

2. The compound of claim 1, or a pharmaceutically acceptable salt thereof, wherein zero, one, or two of $R^{1a}$, $R^{1b}$, $R^{1c}$, and $R^{1d}$ are each independently halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl.

3. The compound of claim 1, or a pharmaceutically acceptable salt thereof, wherein:

(i) one of $R^{1a}$, $R^{1b}$, $R^{1c}$, and $R^{1d}$ is halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl; and (ii) the other three of $R^{1a}$, $R^{1b}$, $R^{1c}$, and $R^{1d}$ are independently H.

4. The compound of claim 1, or a pharmaceutically acceptable salt thereof, wherein:

(i) $R^{1c}$ is halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl; and (ii) $R^{1a}$, $R^{1b}$, and $R^{1d}$ are independently H.

5. The compound of claim 1, or a pharmaceutically acceptable salt thereof, wherein m is 1.

6. The compound of claim 1, or a pharmaceutically acceptable salt thereof, wherein:

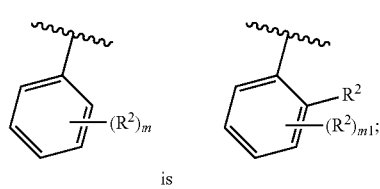

is and m1 is 0 or 1.

7. The compound of claim 1, or a pharmaceutically acceptable salt thereof, wherein each $R^2$ is independently F, Cl, or Br.

8. The compound of claim 1, or a pharmaceutically acceptable salt thereof, wherein:

$R^{3a}$ is X; and $R^{3b}$ is $R^3$.

9. The compound of claim 1, or a pharmaceutically acceptable salt thereof, wherein:

(i) one of $R^{1a}$, $R^{1b}$, $R^{1c}$, and $R^{1d}$ is halo, $NO_2$, CN, $C_{1-6}$ alkyl, $C_{1-6}$ haloalkyl, $C_{2-6}$ alkenyl, $C_{2-6}$ alkynyl, $C(O)R^6$, $C(O)NR^6R^7$, $NR^6R^7$, $Si(C_{1-6}$ alkyl$)_3$, $OC_{1-6}$ alkyl, $OC_{1-6}$ haloalkyl, $SC_{1-6}$ alkyl, $SC_{1-6}$ haloalkyl, $S(NH)(O)C_{1-6}$ alkyl, $S(O)_2C_{1-6}$ alkyl, $C_{3-6}$ cycloalkyl, or $C_{6-10}$ aryl, wherein the $C_{3-6}$ cycloalkyl or $C_{6-10}$ aryl is optionally substituted with 1, 2, 3, or 4 substituents independently selected from the group consisting of halo, CN, $C_{1-6}$ alkyl, and $C_{1-6}$ haloalkyl;

(ii) the other three of $R^{1a}$, $R^{1b}$, $R^{1c}$, and $R^{1d}$ are independently H;

each $R^2$ is independently halo, $NO_2$, CN, $C_{1-6}$ alkyl, $C_{1-6}$ haloalkyl, $C_{2-6}$ alkenyl, $C_{2-6}$ alkynyl, $OC_{1-6}$ alkyl, $OC_{1-6}$ haloalkyl, $S(O)_2C_{1-6}$ alkyl, or $C_{3-6}$ cycloalkyl;

m is 1 or 2;

$R^{3a}$ is X; and $R^{3b}$ is $R^3$.

10. The compound of claim 9, or a pharmaceutically acceptable salt, wherein

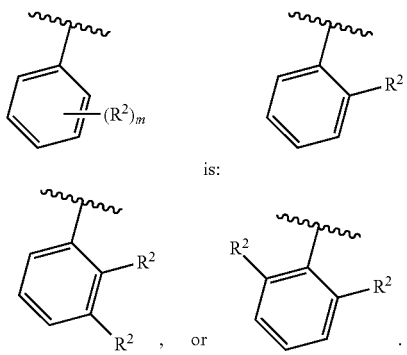

is:

11. The compound of claim 9, or a pharmaceutically acceptable salt thereof, wherein $R^3$ is H.

12. The compound of claim 9, or a pharmaceutically acceptable salt thereof, wherein X is C(O)OH.

13. The compound of claim 9, or a pharmaceutically acceptable salt thereof, wherein:

$R^4$ is H; and $R^5$ is H.

14. The compound of claim 1, or a pharmaceutically acceptable salt thereof, wherein $R^3$ is H.

15. The compound of claim 1, or a pharmaceutically acceptable salt thereof, wherein X is $CH(R^X)C(O)Y$ or C(O)Y.

16. The compound of claim 1, or a pharmaceutically acceptable salt thereof, wherein X is $CH(R^X)C(O)OH$ or C(O)OH.

17. The compound of claim 1, or a pharmaceutically acceptable salt thereof, wherein X is C(O)OH.

18. The compound of claim 1, or a pharmaceutically acceptable salt thereof, wherein:

$R^4$ is H; and $R^5$ is H.

19. The compound of claim 1, wherein the compound is selected from the group consisting of:
1
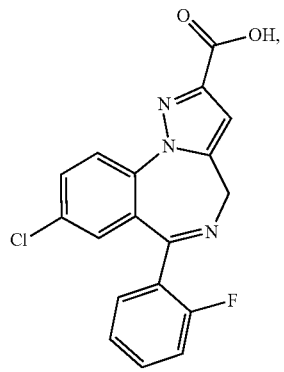
2
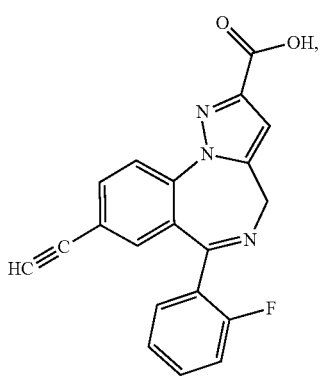
3
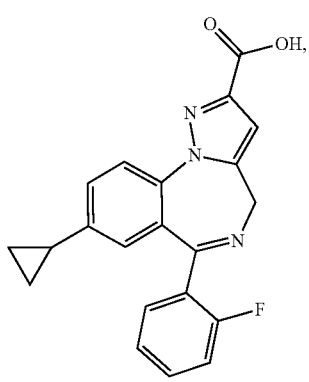
4
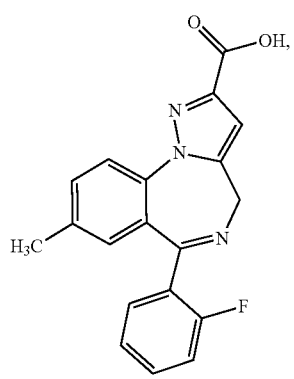
5
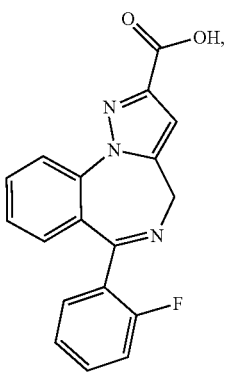
6
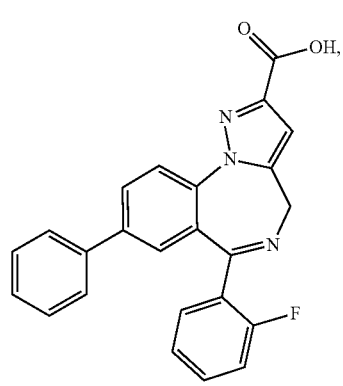
7
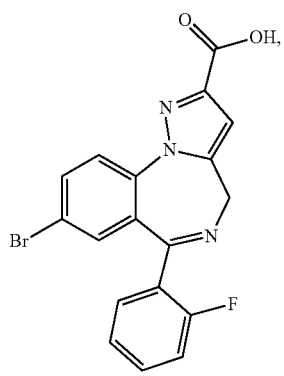
8
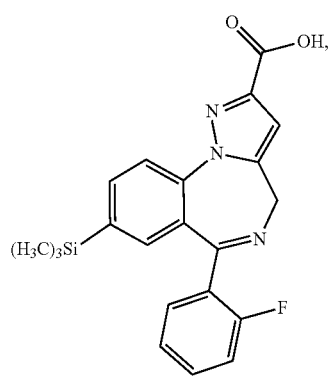

-continued
9
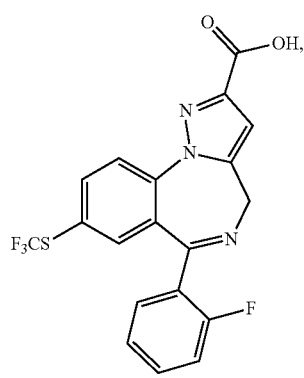
10
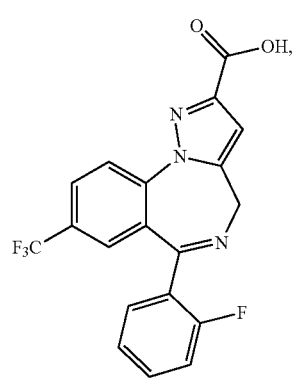
11
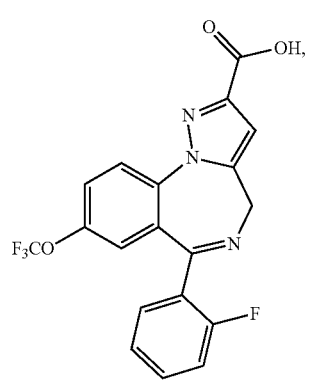
12
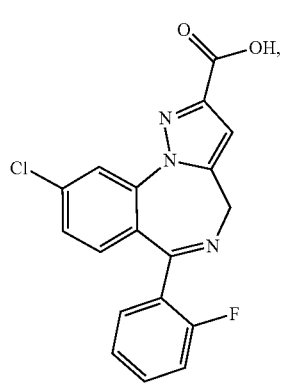
-continued
13
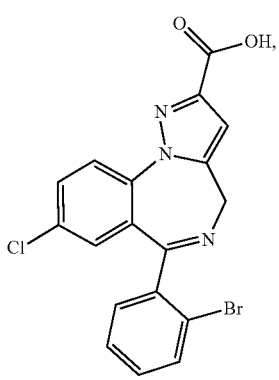
14
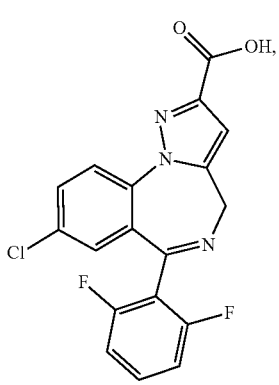
15
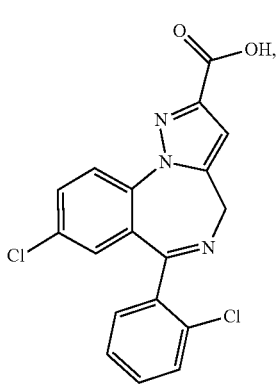
16
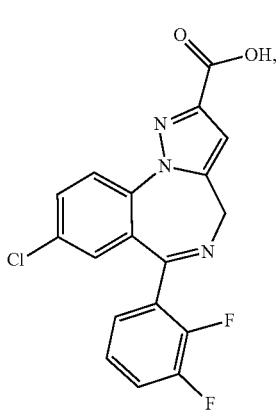

17 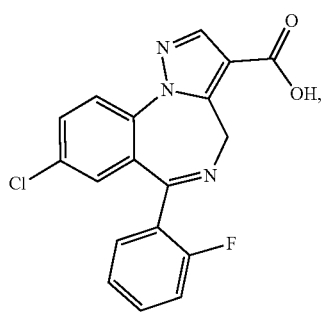

18 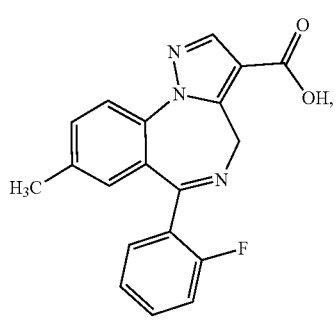

19 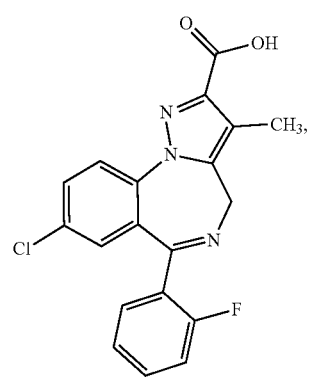

20 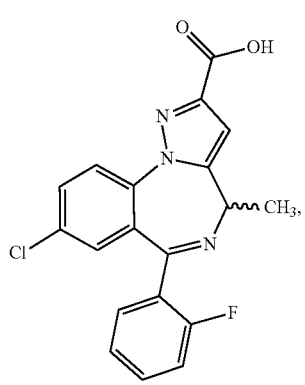

21 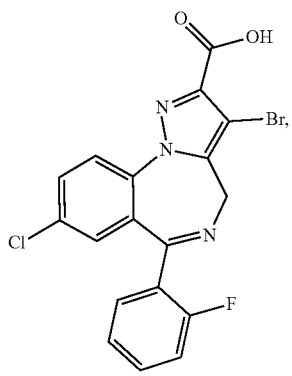

22 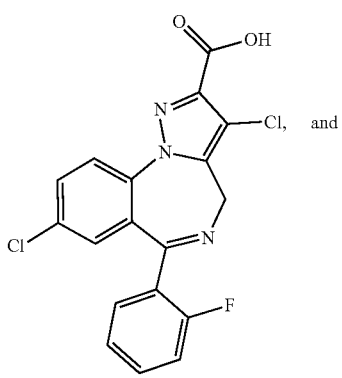

24 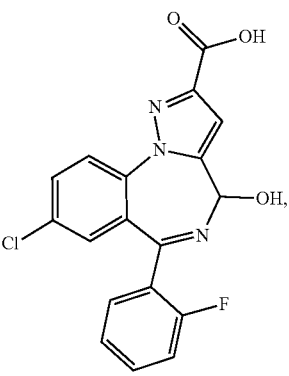

or a pharmaceutically acceptable salt thereof.

20. A pharmaceutical composition comprising a pharmaceutically acceptable carrier and a compound of claim 1, or a pharmaceutically acceptable salt thereof.

21. A method for positively modulating GABA-A receptors in tissues and organs outside the brain and central nervous system in a subject in need thereof, wherein the method comprises administering to the subject a therapeutically effective amount of a compound of claim 1, or a pharmaceutically acceptable salt thereof.

22. The method of claim 21, wherein the subject has a condition or disease selected from the group consisting of bile salt malabsorption, drug induced pain, functional abdominal pain, functional idiopathic diarrhea, an inflammatory bowel disease, lactose intolerance, and visceral pain.

23. The method of claim 21, wherein the subject has irritable bowel syndrome.

24. A method for modulating gut motility in a subject in need thereof, wherein the method comprises administering to the subject a therapeutically effective amount of a compound of claim 1, or a pharmaceutically acceptable salt thereof.
25. A compound selected from the group consisting of:
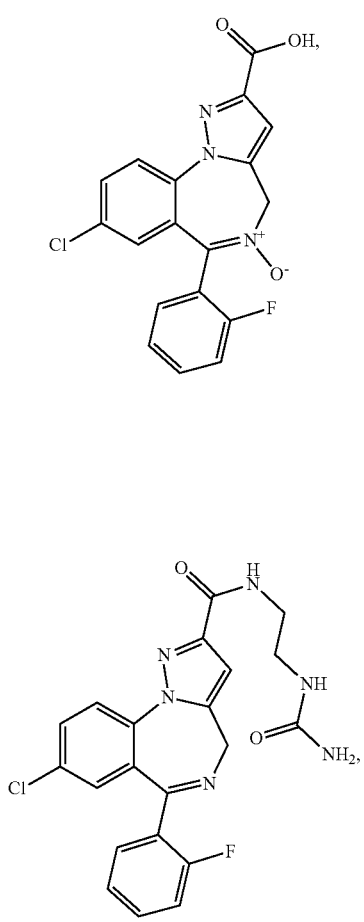
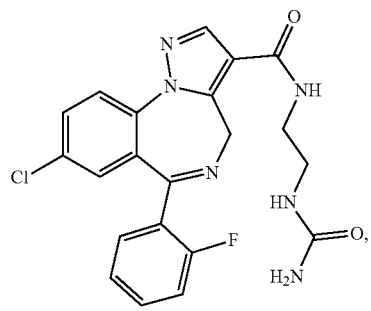
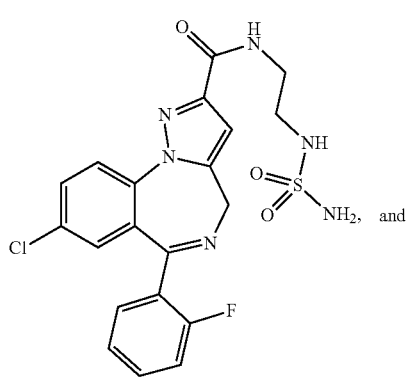
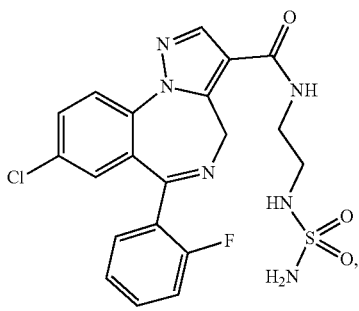
or a pharmaceutically acceptable salt thereof.
* * * * *